(12) United States Patent
Wang et al.

(10) Patent No.: US 9,399,657 B2
(45) Date of Patent: Jul. 26, 2016

(54) CHEMILUMINESCENT METHODS AND REAGENTS FOR ANALYTE DETECTION

(76) Inventors: Tianxin Wang, Boyds, MD (US); Xingxiang Li, Vienna, VA (US)

( * ) Notice: Subject to any disclaimer, the term of this patent is extended or adjusted under 35 U.S.C. 154(b) by 0 days.

(21) Appl. No.: 12/287,916

(22) Filed: Oct. 15, 2008

(65) Prior Publication Data

US 2011/0097753 A1 Apr. 28, 2011

Related U.S. Application Data

(60) Provisional application No. 60/999,166, filed on Oct. 16, 2007.

(51) Int. Cl.
*A61K 31/7056* (2006.01)
*C07H 17/00* (2006.01)
*C07H 15/26* (2006.01)
*C12Q 1/66* (2006.01)
*G01N 33/535* (2006.01)

(52) U.S. Cl.
CPC ............ *C07H 15/26* (2013.01); *A61K 31/7056* (2013.01); *C07H 17/00* (2013.01); *C12Q 1/66* (2013.01); *G01N 33/535* (2013.01)

(58) Field of Classification Search
None
See application file for complete search history.

(56) References Cited

U.S. PATENT DOCUMENTS

| 5,552,298 A | * | 9/1996 | Akhavan-Tafti | ................. 435/28 |
| 2002/0151087 A1 | * | 10/2002 | Hage et al. | ..................... 436/517 |
| 2007/0054342 A1 | * | 3/2007 | Lune et al. | ......................... 435/8 |

OTHER PUBLICATIONS

Sasamoto et al., Chem. Pharm. Bull. 38(5) 1323-1325 (1990).*

* cited by examiner

*Primary Examiner* — Alicia L Otton

(57) ABSTRACT

The present invention relates to chemiluminescent method and regent to detect analyte. One aspect of the current invention relates to using enzyme substrate that can be cleaved by target enzyme to release chemiluminescent compound giving light signal for the detection of varieties of target enzymes. Another aspect of the current invention relates to use chemiluminescent enzyme coupled with analyte binding molecules to detect specific analyte molecules in a homogenous phase.

3 Claims, 13 Drawing Sheets

R1, R2, R3, R4 = H or alkyl group

SEQUENCE LISTING

```
<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: random sequence used as affinity ligand

<400> SEQUENCE: 1
cccccccccc cc                                                        12

<210> SEQ ID NO 2
<211> LENGTH: 12
<212> TYPE: DNA
<213> ORGANISM: Artificial Sequence
<220> FEATURE:
<223> OTHER INFORMATION: random sequence used as affinity ligand

<400> SEQUENCE: 2
gggggggggg gg                                                        12
```

CHEMILUMINESCENT METHODS AND REAGENTS FOR ANALYTE DETECTION

CROSS-REFERENCE TO RELATED APPLICATION

This application claims priority to U.S. Provisional Application No. 60/999,166 filed on Oct. 16, 2007. The entire disclosure of the prior application is considered to be part of the disclosure of the instant application and is hereby incorporated by reference.

TECHNICAL FIELD

The present invention relates to chemiluminescent method and regent to detect analyte. One aspect of the current invention relates to using enzyme substrate that can be cleaved by target enzyme to release chemiluminescent compound giving light signal for the detection of varieties of target enzymes. Another aspect of the current invention relates to using chemiluminescent enzyme coupled with analyte binding molecules to detect specific analyte molecules in a homogenous phase.

BACKGROUND OF THE INVENTION

Advances in the biological, biomedical and pharmaceutical sciences have accelerated the pace of research and diagnostics to a level unparalleled to the past. With sequences of whole genome becoming available quickly and successively, the assembly of large libraries of small molecules, the ability to move pharmaceutical development, clinical diagnostic tests and basic research from a reductionist to a whole system approach quickly all demand assays that facilitate high throughput analyses. Chemiluminescence (sometimes "chemoluminescence") is the emission of light (luminescence) with limited emission of heat as the result of a chemical reaction. Light-emitting systems have been known and isolated from many luminescent organisms, including certain bacteria, protozoa, coelenterates, mollusks, fish, millipedes, flies, fungi, worms, crustaceans, and beetles. Those enzymes isolated from beetles, particularly the fireflies of the genera *Photinus, Photuris* and *Luciola* and click beetles of genus *Pyrophorus* have found widespread use in reporter systems. In many of these organisms, enzymatically catalyzed oxidoreductions take place in which the free energy change is utilized to excite a molecule to a high-energy state. When the excited molecule spontaneously returns to the ground state, visible light is emitted. This emitted light is called "bioluminescence" or "chemoluminescence". Luminescent luciferase-based assays have been developed to monitor or measure kinase activity, P450 activity, and protease activity. Firefly luciferase or click beetle luciferase catalyses the oxidation of firefly luciferin in the presence of ATP, $Mg^{2+}$ and molecular oxygen with the resultant production of light. This reaction has a quantum yield of about 0.88 and this light emitting property has led to its use in luminescent assays. There are also other types of luciferin that can trigger luminescent reaction. Bacterial luciferin is a reduced riboflavin phosphate (FMNH2, pictured here), which is oxidized in association with a long-chain aldehyde, oxygen, and a bacterial luciferase. Dinoflagellate luciferin is derived from chlorophyll, and has a very similar structure. In the genus Gonyaulax, at pH 8 the molecule is "protected" from the luciferase by a "luciferin-binding protein", but when the pH lowers to around 6, the free luciferin reacts and light is produced. Vargulin is found in the ostracod ("seed shrimp") Vargula, and is also used by the midshipman fish Porichthys. Here there is a clear dietary link, with fish losing their ability to luminesce until they are fed with luciferin-bearing food. Coelenterazine is the most "popular" of the marine luciferins, found in a variety of phyla. This molecule can occur in luciferin-luciferase systems, and is famous for being the light emitter of the photoprotein "aequorin". Besides enzyme-catalyzed chemoluminescence, small organic molecule based chemiluminescence assays are also widely used for analyte detection. The most important chemiluminescent compounds include luminol, acridinium and 1,2-dioxetane.

SUMMARY OF THE INVENTION

The present invention relates to chemiluminescent reagent and methods for analyte detection.

These reagents and methods disclosed in the present invention enable simple, rapid and sensitive detection of the analyte.

One aspect of the current invention involves the use of the chemiluminescent compound-enzyme substrate conjugate to detect the presence of target enzyme. The enzyme breaks the conjugate and releases the chemiluminescent compound. The chemiluminescent compound can emit detectable light under suitable conditions and therefore indicate the presence of certain target enzyme. The chemiluminescent compounds used in the current invention are firefly luciferin or 1,2-dioxetane. The enzyme can be detected include alpha-L-Arabinosidase, beta-Cellobiosidase, alpha-L-Fucosidase, beta-D-fucosidase, beta-L-Fucosidase, alpha-Galactosaminidase, beta-Galactosaminidase, alpha-Galactosidase, beta-Galactosidase, alpha-Glucosaminidase, beta-Glucosaminidase, alpha-Glucosidase, beta-Glucosidase, beta-Glucuronidase, beta-Lactosidase, alpha-Maltosidase, alpha-Mannosidase, beta-Mannosidase, beta-Xylosidase, neuraminidase, proline aminopeptidase, leukocyte esterase, alpha-L-fucosidase, glycylproline dipeptidyl aminopeptidase, beta-galactosaminidase, N-acetyl-beta-D-glucosaminidase, Salmonella esterase, beta-glucuronidase and hydroxyproline aminopeptidase.

Another aspect of the present invention provides methods and compositions for firefly luciferase based homogeneous enzyme channeling luminescent assays for analyte detection. The disclosed invention utilizes the enzyme channeling effect to detect the analyte therefore enable simple, rapid and sensitive detection of the analyte without any separation steps. In some embodiments, the two enzymes utilized for enzyme channeling are firefly luciferin producing enzyme and firefly luciferase. In other embodiments, those two enzyme utilized are ATP producing enzyme and firefly luciferase.

DETAILED DESCRIPTION OF THE INVENTIONS

Figure 1:
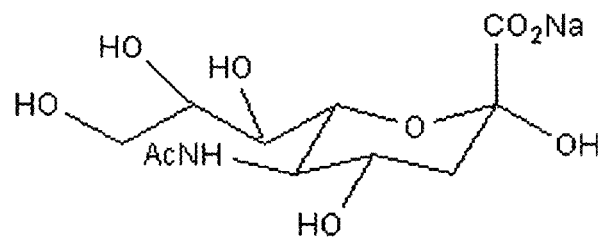
FIG. 1 is the chemical structure of N-acetylneuraminic acid.
Figure 2:
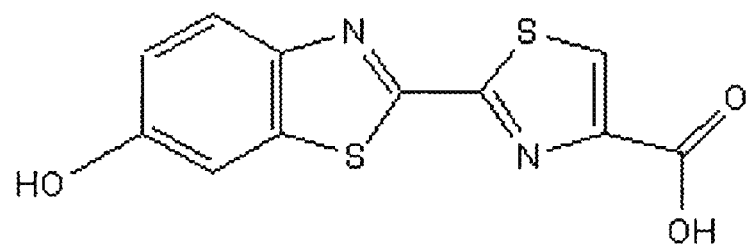
FIG. 2 is the chemical structure of firefly luciferin.
Figure 3:
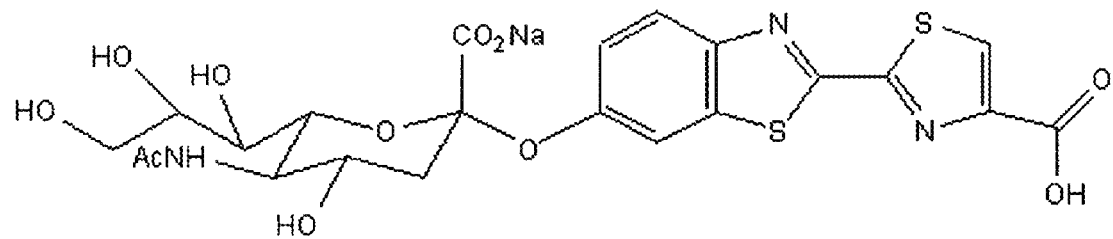
FIG. 3 is a chemical structure of an N-acetylneuraminic acid-firefly luciferin conjugate.

The conjugate of N-acetylneuraminic acid (FIG. 1) and firefly luciferin (FIG. 2) is substrate for neuraminidase. N-acetylneuraminic acid is also called sialic acid. A number of organisms express neuraminidase that can hydrolyze the N-acetylneuraminic acid-firefly luciferin conjugate (FIG. 3). For example, influenza virus, parainfluenza and certain bacterial species possess neuraminidases. One important aspect of the current invention is the use of N-acetylneuraminic acid-firefly luciferin conjugate for specific detection of a neuraminidase from a particular organism.

According to one embodiment of the invention, in order to detect certain species of neuraminidase activity, the undesired interfering neuraminidase activity from other species is inhibited using specific polyclonal or monoclonal antibodies. For example, for detection of influenza viral neuraminidase, the non-specific neuraminidase activity from likely contaminating organisms in the sample such as bacterial species *Streptococcus pneumoniae* and *Actinomyces viscosus* are inhibited using antibodies specific for the neuraminidases from these sources. This approach is possible because neuraminidases from different organisms have distinct amino acid sequences, which permits the generation of species-specific, or sub-species-specific, neuraminidase antibodies. For example, specific antibodies are commonly used to differentiate neuraminidase types of influenza virus in neuraminidase neutralization assays.

The procedure of making these antibodies is well to the skilled in the art. For example, recombinant neuraminidase protein can be produced in *E. coli* by cloning the complete or partial genomic (in the case of bacterial neuraminidase) or cDNA (in the case of eukaryotic neuraminidase) sequences into a bacterial expression vector that preferably contains an affinity ligand, e.g., his-tag, which facilitates the purification of the recombinant protein. Bacterial clones expressing the enzyme can be screened and selected in a chemiluminescence assay using the N-neuraminic acid-firefly luciferin conjugate. If the recombinant enzyme is tagged with an affinity ligand, then appropriate affinity column can be used to purify the enzyme. For example, nickel coated agarose column can be used to purify his-tagged recombinant neuraminidase. The purified neuraminidase can be used to immunize an animal, e.g., a rabbit, for production of polyclonal antibodies. Alternatively, the protein can be used to immunize mouse from which the B-lymphocytes can be used to generate hybridoma, which can be used for screening a monoclonal antibody that specifically inhibits the neuraminidase.

One or more monoclonal and/or polyclonal antibodies can be used in an assay for inhibiting neuraminidase activities from one or more contaminating sources. For example, polyclonal antibodies or anti-sera or monoclonal antibodies for *Streptococcus pneumoniae, Actinomyces viscosus* and parainfluenza neuraminidases can be used in an assay for detecting influenza viral neuraminidase. It is understood that the amounts of each antibody or anti-serum used in an assay need to be optimized so that the antibodies can maximally inhibit contaminating neuraminidase activities but not the neuraminidase activity to be detected.

This method can be generalized for the detection of specific enzyme. For example, if enzyme A and B use the same substrate, in order to selectively detect enzyme B in the presence of enzyme A, the antibody against enzyme A activity but not against enzyme B activity can be added to the assay based on the detection of enzyme activity to decrease the interference from enzyme A.

Besides fire fly luciferin, coelenterates type luciferin can also be used to synthesize a glycoside with sialic acid or its derivatives via the phenol group on coelenterates. This kind of glycosides is also appropriate for use in the detection of neuraminidase activity, using a procedure similar to the detection of neuraminidase.

Figure 4:
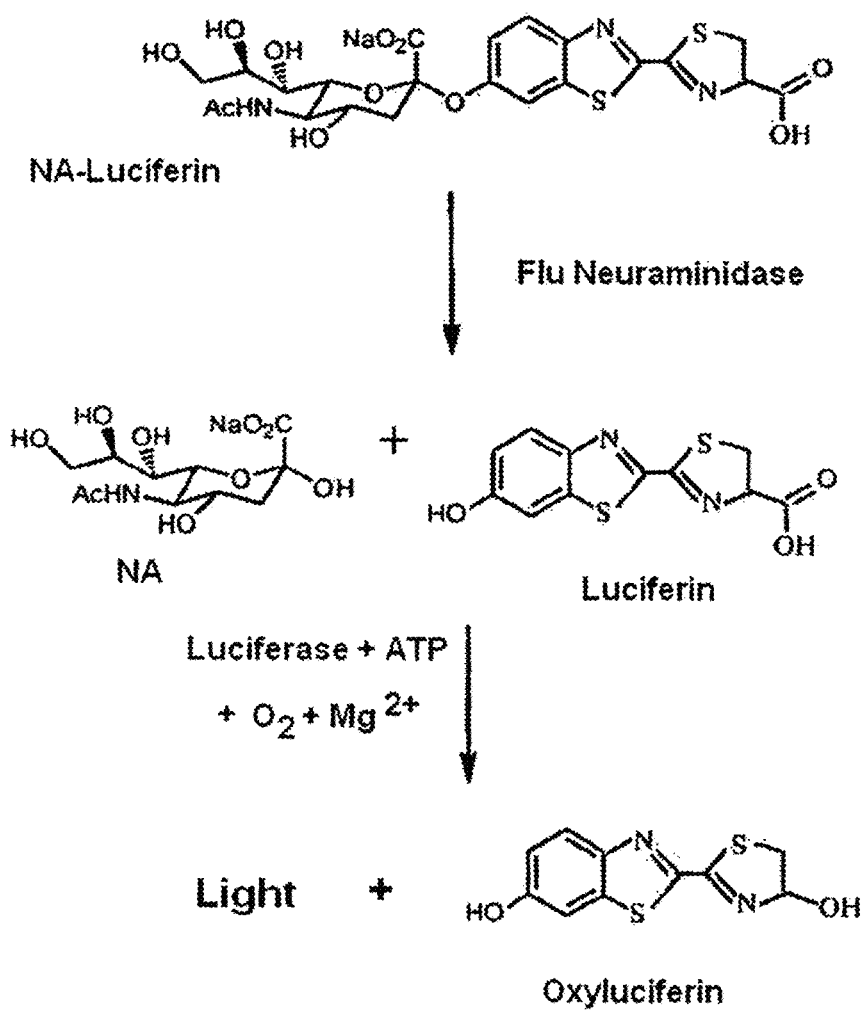
FIG. 4 provides a schematic drawing showing the principle for influenza neuraminidase detection as a means for the detection of influenza virus using the N-acetylneuraminic acid-firefly luciferin conjugate.

The principle for detecting neuraminidase activity using the conjugate is depicted in FIG. 4. The sialic acid-firefly luciferin conjugate is a substrate for neuraminidase, which cleaves the substrate to give rise to free firefly luciferin that is the substrate of luciferase, which is present in the detection mix. The conjugate itself is not a substrate for firefly luciferase. Therefore, the luciferase-catalyzed biochemiluminescence is dependent on neuraminidase activity, which is provided by the influenza virus or other organisms to be detected. As described above, specificity of the assay can be achieved through the use of inhibiting antibodies or modification of the sialic acid moiety of the conjugate. The drawing shows the principle for neuraminidase (e.g. influenza neuraminidase) detection as a means for the detection of influenza virus using the N-acetylneuraminic acid-firefly luciferin conjugate. However, the same principle works for the neuraminidase from other species using the same substrate. Further more, the same principle also works for other enzyme when suitable chemiluminescent substrate is used as long as the substrate can be cleaved by the target enzyme and the cleavage product can emit light for detection.

The assay can be done in one step or two-step fashion. The two-step assay separates the enzyme cleavage step with the chemiluminescent step. The key feature of one-step method is the combination of target enzyme (e.g. neuraminidase) reaction with the chemiluminescence reaction in a single step. In this assay format, luciferin is detected as it is being released through the action of target enzyme (e.g. neuraminidase).

This method is therefore referred to as real time detection of target enzyme (e.g. neuraminidase) or real time detection method. However, in the real time enzyme detection method, the detection mix contains all necessary chemicals and appropriate buffer for target enzyme reaction, including the conjugate itself, and for luciferase-catalyzed chemiluminescence reaction except for luciferin.

In the current invention, the term chemiluminescence and bioluminescence are used interchangeable. Luciferin and luciferase are not specific molecules. They are generic terms for a substrate and its associated enzyme (or protein) that catalyze a light-producing reaction. A variety of species regulate their light production using different luciferases in a variety of light-emitting reactions. Luciferins are a class of small-molecule substrates, each being specific for its corresponding protein enzyme luciferase. Luciferins are catalyzed in the presence of the enzyme luciferase to produce light.

In the current inventions described above and below, the term firefly luciferase include both the native firefly luciferase extracted from firefly and those engineered firefly luciferase such as those generated by mutation for better thermal stability or different optimum pH or emission wavelength. There are many engineered firefly luciferase that can be found in scientific publications and patents and many of them are commercially available. Any firefly luciferase is suitable for the current invention as long as it uses firefly luciferin or firefly luciferin directives (e.g. 6-amino firefly luciferin) for luminescence. Since there are also other luciferases that utilize firefly luciferin to emit light, for example, the click beetle luciferase, these luciferases can also be used to replace the firefly luciferase used in the current invention.

There are several general types of luciferins: Firefly luciferin is the luciferin found in fireflies. It is the substrate of firefly luciferase. Bacterial luciferin is a type of luciferin found in bacteria, some squid and fish. It consists of a long-chain aldehyde and a reduced riboflavin phosphate. Dinoflagellate luciferin is a chlorophyll derivative and is found in dinoflagellates, which are often responsible for the phenomenon of nighttime ocean phosphorescence. A very similar type of luciferin is found in some types of euphausiid shrimp. Another luciferin called vargulin is found in certain deep-sea fish, specifically, in ostracods and porichthys. It is an imidazolopyrazine. The fifth luciferin called coelenterazine is found in radiolarians, ctenophores, cnidarians, squid, copepods, chaetognaths, fish and shrimp. It is the light-emitting molecule in the protein called aequorin. Yet another luciferin is called latia luciferin which can be found in sea latia neritoides.

Figure 5:
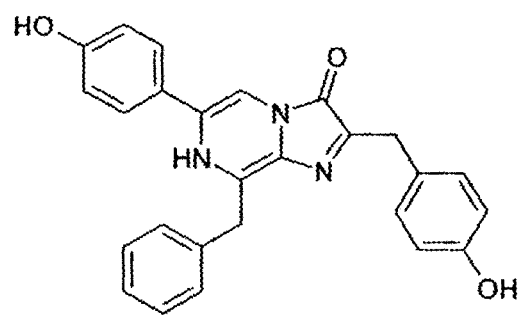
FIG. 5 is chemical structure of coelenterazine.
Figure 6:
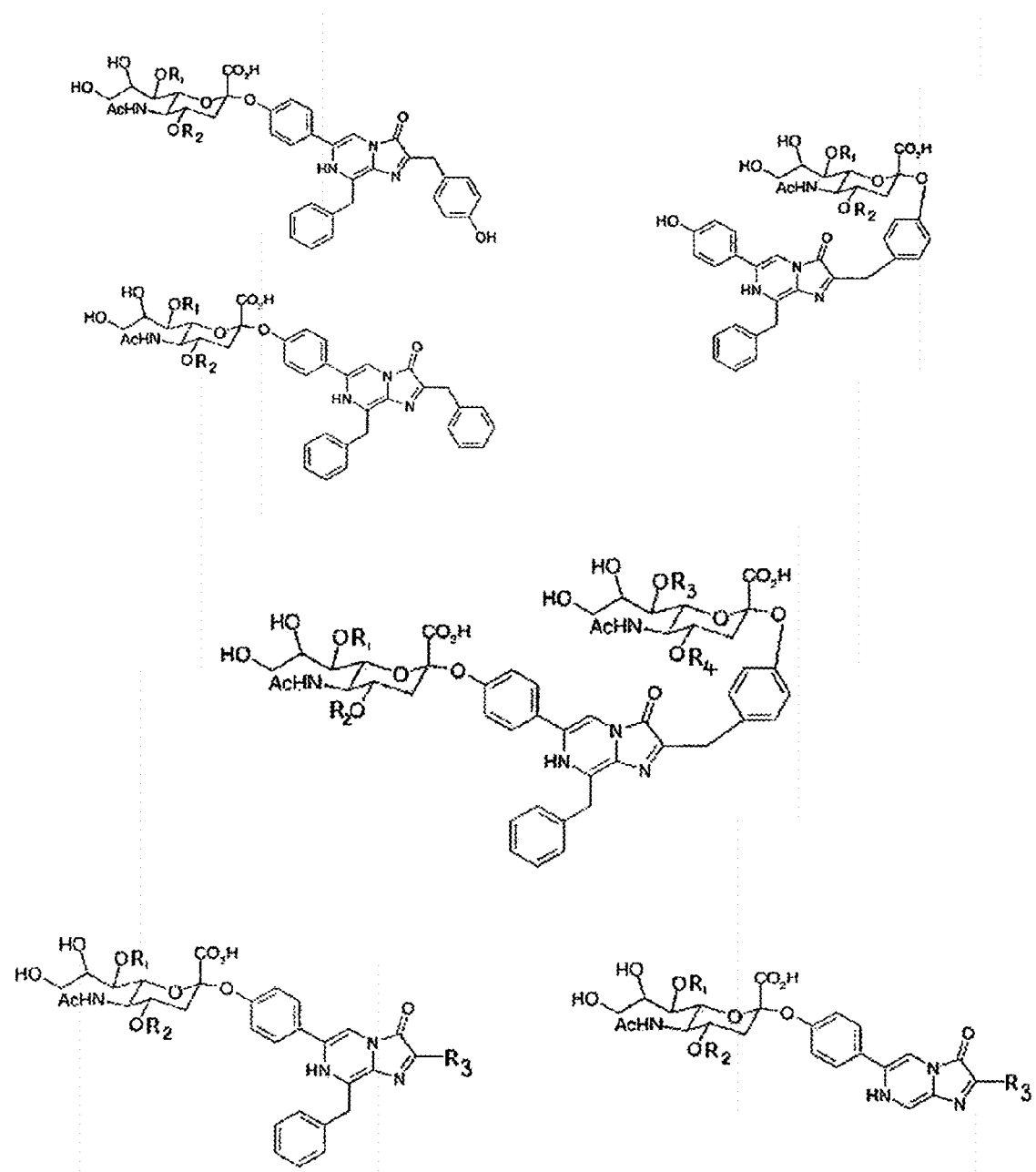
FIG. 6 provides coelenterazine (or its derivatives)—N-acetylneuraminic acid conjugate as substrate for sialidase detection, where R1, R2, R3, R4=H or alkyl group such as methyl group.

The luciferins suitable in the current invention are firefly luciferin and coelenterazine (FIG. 5). The coelenterazine-sialic acid conjugate can also be cleaved by sialidase and the released coelenterazine can produce light signal under the presence of aequorin. FIG. 6 provides the structures of a list of coelenterazine (or its derivatives)—N-acetylneuraminic acid conjugates, which can be used as substrates in a sialidase assay such as Flu test or bacterial vaginosis test described below.

The methods, reagents and kits described above can also be used for detection of other sialidases of bacterial, viral, protozoa, and vertebrate (including human) origin besides sialidase from influenza virus. Sialidase (also known as neuraminidase or acylneuraminyl hydrolase) is a protein enzyme produced by many organisms such as bacteria, viruses, protozoa, and vertebrates including humans. This class of enzymes catalyzes the hydrolysis of terminal sialic acids which are alpha-ketosidically linked to glycoproteins, glycolipids, and polysaccharides through an O-glycosidic bond. There are a large number of biological functions ascribed to sialidase enzyme, including cell-cell recognition and pathogenicity of some infections by sialidase-bearing microorganisms.

In bacteria, sialidase helps bacterial adhesion to tissues and generates additional nutritional sources. In the case of the influenza virus, sialidase is one of two surface glycoproteins and is considered to be important for both transporting the virus through mucin and for the budding of virus progeny from the infected cells. In the parasite *Trypanosoma cruzi*, a sialidase (also known as trans-sialidase) removes sialic acids from the infected cells and decorates its own surface with these sialic acids. In humans, sialidases are involved in protein degradation, immune responses, and cell proliferation. Abnormal production of sialidases may lead to serious human diseases such as sialidosis or increased *Pseudomonas aeruginosa* infection in cystic fibrosis patients.

Since sialidases are associated with many diseases, a chemiluminescent substrate (e.g., the N-acetylneuraminic acid-firefly luciferin conjugate described above) of sialidase would be an excellent diagnostic or prognostic reagent for sialidase-related diseases. For instance, sialidase level is elevated in bacterial vaginosis. Measurement of sialidase level in the vaginal samples such as vaginal fluids can be used to diagnose bacterial vaginosis. Therefore, the kits and reagents and methods described above can also be used to diagnose bacterial vaginosis.

Figure 7:
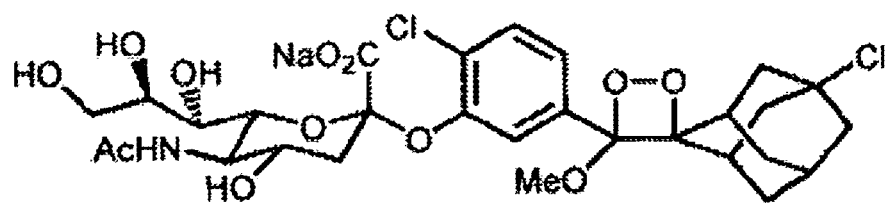
FIG. 7 provides an example of 1,2-dioxetane-sialic acid conjugate as substrate for sialidase detection used in bacterial vaginosis test or Chagas disease.
Figure 8:
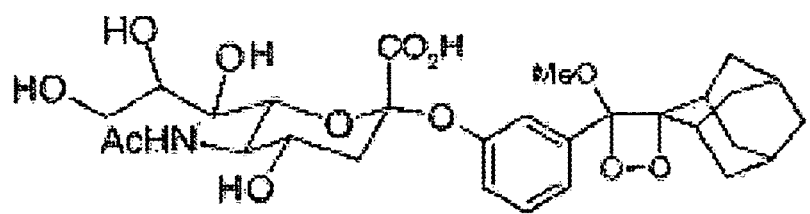
FIG. 8 provides additional examples of 1,2-dioxetane-sialic acid conjugates and derivatized forms of the conjugates as substrates for sialidase detection used in bacterial vaginosis test or Chagas disease test.
Figure 8:
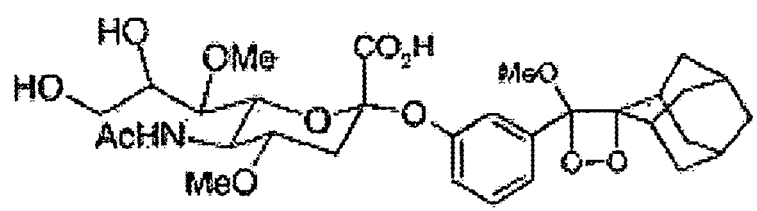
Figure 8:
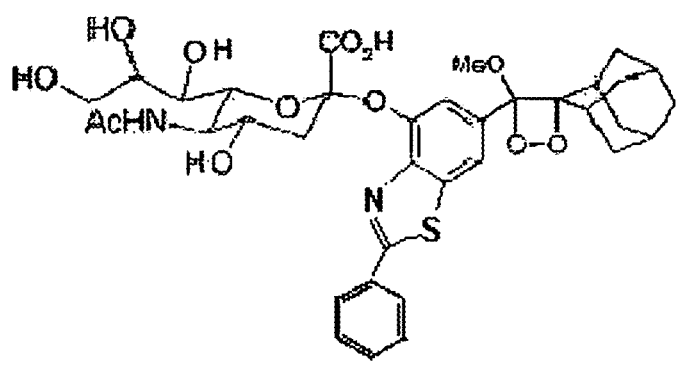

In addition to the luciferin—N-acetylneuraminic acid conjugate, the chemiluminescent dioxetane-sialic acid conjugates, or its variations, are also suitable for use in the diagnosis of bacterial vaginosis, Chagas disease, or other diseases and conditions where sialidase is an appropriate marker. The structures for some of the substrates are shown in FIG. 7 and FIG. 8. It is understood that variations of these conjugates may (e.g. the dioxetane can be selected from the dioxetane described in U.S. Pat. Nos. 7,081,352 and 6,555,698) also be appropriate for detecting sialidase as the marker.

Substrates depicted in FIGS. 7 and 8 or similar substrates can be synthesized using protocols that are described in U.S. Pat. Nos. 7,081,352 and 6,555,698 as well as in a publication (Analytical Biochemistry 2000; 280, 291-300). Hydroxyl groups at the 4' and 7' positions of the sialic acid moiety is preferred for detection of bacterial sialidase since the 4, 7 alkylated substrates are more specific to viral sialidase.

Chagas' disease (also called American trypanosomiasis) is a human tropical parasitic disease, which occurs in the Americas, particularly in South America. Its pathogenic agent is a flagellate protozoan named *Trypanosoma cruzi*, which is transmitted to humans and other mammals mostly by blood-sucking bugs of the subfamily Triatominae (Family Reduviidae). The cell invasion form of *T. cruzi*, Trypomastigote, expresses high levels of trans-sialidase activity; therefore, measurement of sialidase level can be used for diagnosis of active *T. cruzi* infection and for monitoring disease or therapeutic progress.

The substrates described above can also be used for the diagnosis of *T. cruzi* infection and Chaga's disease. As in the bacterial vaginosis diagnostic tests, either N-acetylneuraminic acid-luciferin or N-acetylneuraminic acid-dioxetane conjugate, including their derivatives, can be used for detection of *T. cruzi* infection. *T. cruzi* infection can be diagnosed with an assay that uses either N-acetylneuraminic acid-luciferin or N-acetylneuraminic acid-dioxetane conjugate. There are several different types of infection status: 1) acute infection, which is an acute phase of an infection, 2) chronic active infection, which an infection with persistent and active infection, and 3) cleared or dormant infection, which is an infection without active infection but with detectable antibodies specific for the protozoa.

For diagnosis of acute and active or chronic infection, sialidase activity in plasma or serum is measured using the chemiluminescent assay described in this invention. Elevated sialidase activity in plasma or serum indicates active *T. cruzi* infection. In an active infection assay, serum or plasma sample with appropriate dilution in a buffer (e.g., PBS buffer) as determined with experiments is added to a detection mix as described in Example 2. The detection mix is preferably lyophilized for long-term storage. The output signal is then measured with a luminometer. Again, a cutoff value for diagnosis positive needs to be established by testing a large number of negative samples, e.g., 100 or more of negative samples. Sensitivity of the assay can be determined by testing a large number of positive samples, e.g., 100 or more of positive samples confirmed with another method such as polymerase chain reaction (PCR) method.

*T. cruzi* infection may be cleared by the host but still results in detectable antibodies, which can be detected with a neutralization assay that uses the same detection mix as for an active infection test except that the detection mix also contains small amounts of *T. cruzi* sialidase. In the absence of specific antibodies in a serum or plasma sample, the *T. cruzi* sialidase in the detection mix generates a detectable light signal at certain level. In the presence of specific antibodies in a serum or plasma sample, a reduction of the signal can be detected. Thus, a reduction of the signal indicates chronic, cleared or dormant infection. Again, a cutoff value needs to be established by testing a large number of negative samples, e.g., 100 or more of negative samples. Sensitivity of the assay can be determined by testing a large number of positive samples, e.g., 100 or more of positive samples confirmed with another method such as an ELISA test.

In order to block the activity of human endogenous sialidase in the sample, which may interfere the measurement of *T. cruzi* sialidase activity, suitable amount of antibody against human endogenous sialidase, which can block its catalytic activity, can be added to the reaction mix. However, this antibody should not block the activity of the sialidase of *T. cruzi*.

In periodontal disease caused by bacterial infection, it has been shown that the presence of sialidase increases the colonization of harmful bacteria. In cystic fibrosis patients, *Pseudomonas aeruginosa* infection is one of the leading causes of death. Sialidase was shown to be involved in the disease progress. Sialidase is also related to the regulation of cell proliferation, the clearance of plasma proteins, and the catabolism of gangliosides and glycoproteins. Therefore, the reagent and method used for bacterial vaginosis described in the current invention can also be used for the diagnosis for these conditions.

Elevated proline aminopeptidase activity in vaginal fluid has been associated with bacterial vaginosis. Thus, a proline aminopeptidase assay can also be used to diagnose bacterial vaginosis. Proline aminopeptidase (or called proline iminopeptidase) is a hydrolase that cleaves the L-proline residues from the N-terminal position in peptides. A substrate that can be used in a proline aminopeptidase assay for bacterial vaginosis diagnosis is L-proline-6-amino firefly luciferin conjugate (L-prolyl-6-amino firefly luciferin, FIG. 9) or its derivatives. In a proline aminopeptidase assay, the enzyme cleaves the synthetic substrate (FIG. 9) and releases the free 6-amino firefly luciferin, which can be quantitatively detected in a chemiluminescence reaction in the presence of firefly luciferase and ATP. It can be a one-step assay or two step assays in a fashion similar to those described in the influenza or bacterial vaginosis sialidase assay. One skilled in the art can readily transfer the reagent and method used in the bacterial vaginosis sialidase assay for the proline aminopeptidase assay by replacing the substrate.

Figure 10:
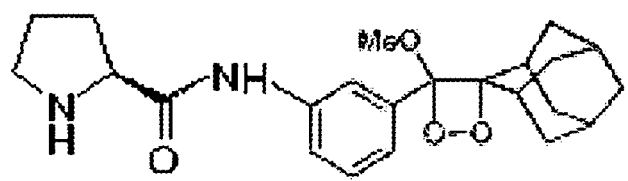
FIG. 10 shows an example of L-prolyl-amino dioxetane.

In other embodiments, L-proline-1,2-dioxetane derivative conjugates, illustrated in FIG. 10 as an example, are used in a chemiluminescent proline aminopeptidase assay for detection of bacterial vaginosis. Instead of using 6-amino firefly luciferin as the chemiluminescent moiety, these conjugates use amine containing dioxetane derivative (such as those listed in U.S. Pat. No. 5,843,681) as the chemiluminescent moiety, which is conjugated to the —COOH group of L-proline through a peptide bond as shown in FIG. 10 as an example. Synthesis of this group of conjugates can be accomplished using peptide synthesis chemistry, which is well known to the skilled in the art.

Detection protocols for the chemiluminescent proline aminopeptidase assay can be adopted from those described in Example 4 when L-proline-luciferin is used as the substrate. The peptidase assay protocol can also be adopted from well know resource (e.g. U.S. Pat. No. 5,843,681) by the skilled in the art when L-proline-dioxetane is used as the substrate. Again, a cutoff value needs to be established by testing a large number of negative samples, e.g., 100 or more of negative samples. Sensitivity of the assay can be determined by testing a large number of positive samples, e.g., 100 or more of positive samples.

Figure 11:
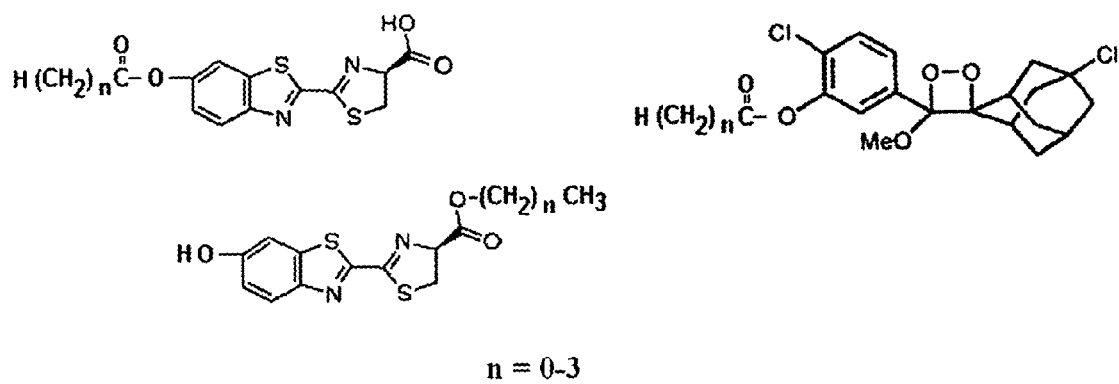
FIG. 11 shows examples of substrates suitable for LE activity detection.

Elevated leukocyte esterase activity indicates the presence of white blood cells and other abnormalities associated with infection or inflammation. Leukocyte esterase test (LE test) is widely used to detect a leukocyte esterase, an enzyme released by white blood cells, which suggests the presence of leukocytes (white blood cells) in the sample, e.g. LE in the urine, which in turn probably indicates active urinary tract infection. LE tests are also used to screen for gonorrhea infection, colpitis, amniotic fluid infections, bacterial meningitis, and ascite or hydrothorax infection by testing leukocyte esterase activity in appropriate samples. Current invention involves chemiluminescent substrates and methods for leukocyte esterase test. The substrates are carboxylic acid—firefly luciferin conjugates such as acetyl firefly luciferin. The —COOH group of the carboxylic acid are coupled with the 6-OH group of the firefly luciferin to generate an ester bond. Suitable carboxylic acids include, but are not limited to, alkyl substituted carboxylic acid such as formic acid, acetic acid, propionic acid, butyric acid and etc. as well as aromatic acid such as benzoic acid. The esterase hydrolyzes the ester bond of the conjugate to release free firefly luciferin, which becomes a substrate for luciferase in a biochemiluminescent reaction that generates a light signal. Alternatively, the carboxylic acid-1,2-dioxetane conjugates are also suitable substrates for chemiluminescent LE activity detection. These dioxetane conjugates can be structurally similar to those that are depicted in FIGS. 7 and 8, where the sugar moiety (N-acetylneuraminic acid) is replaced with the carboxyl group, e.g. an acetyl group, to form an ester bond. In still certain embodiments, the substrate are the firefly luciferin-alcohol conjugates, which is the ester formed by coupling the —COOH group of firefly luciferin with the —OH of an alcohol, resulting in, for example, firefly luciferin methyl ester or firefly luciferin ethyl ester. The alcohol can be either alkyl alcohol such as methanol, glycerol or aromatic alcohol such as benzyl alcohol. The esterase hydrolyzes the ester bond of the conjugate to release free firefly luciferin, which becomes a substrate for luciferase in a biochemiluminescent reaction that generates a light signal. Elevated light signal indicates high LE activity, which in turn is indicative of an active infection. Three examples suitable for LE activity detection is shown in FIG. 11, where n could be any integers between 0 and 3. Again, a cutoff value needs to be established by testing a large number of negative samples, e.g., 100 or more of negative samples. Sensitivity of the assay can be determined by testing a large number of positive samples, e.g., 100 or more of positive samples.

Figure 12:
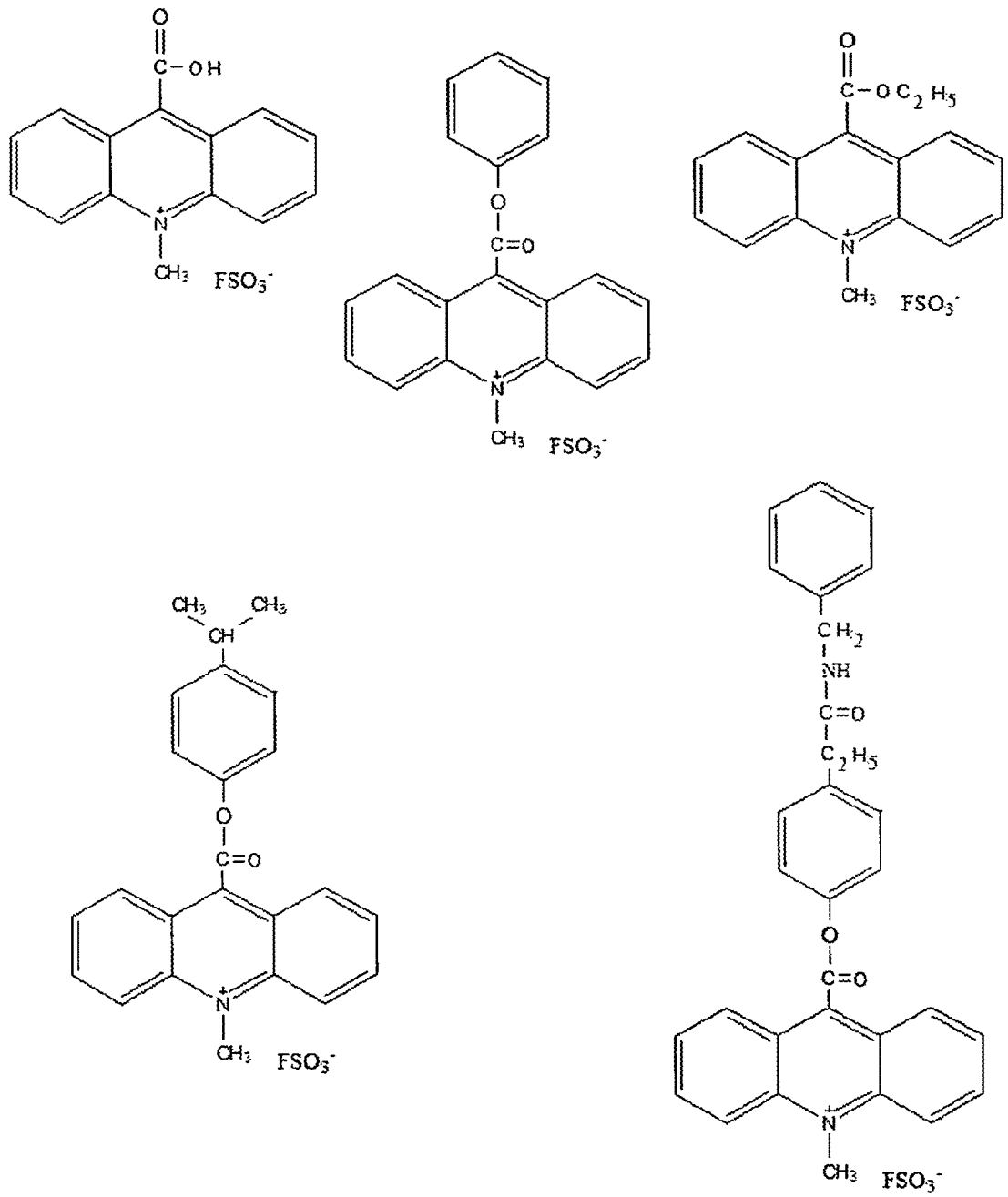
FIG. 12 shows examples of chemiluminescent acridinium derivatives.

Hydrogen peroxide ($H_2O_2$) producing lactobacilli play an important role in preventing vaginal infections by controlling the microbial flora in vagina. Women colonized by lactobacilli have decreased acquisition of vaginal infections because the $H_2O_2$ produced inhibits the growth of pathogenic bacteria. A test that can quantitatively detect $H_2O_2$ in the vaginal sample can be used to assess the health of vaginal microenvironment and for the diagnosis of bacterial vaginosis and other vaginosis such as yeast infection. The test described in the current invention utilizes a chemiluminescent substrate that can generate a light signal when mixed with $H_2O_2$. Examples of suitable substrates include acridinium derivatives and luminol. Examples of some acridinium derivatives are shown in FIG. 12. A variety of acridinium derivatives including amine-derivatized, carboxyl-derivatized and NHS ester derivatized acridinium are commercially available or can be found from a well-known reference. It is understood that other $H_2O_2$ dependent chemiluminescent chemicals, known or unknown, may be appropriate for detecting hydrogen peroxide in vaginal fluid samples as an indicator for vaginal infection status so long as the chemiluminescent chemicals enable a chemiluminescent reaction that is dependent on hydrogen peroxide. Elevated pH (e.g. pH=8~11) or the presence of peroxidase (e.g. horse radish peroxidase) increase the release speed of active oxygen from $H_2O_2$. The released active oxygen causes the acridinium or luminol to undergo oxidation and emit light that can be detected with a luminometer. Therefore assay conditions such as elevated pH (e.g. pH=8~11) or addition of peroxidase can increase the light signal in the $H_2O_2$ detection assay. The optimal peroxidase amount need to be added or the optimal pH can be determined experimentally according to protocols that are well known to the skilled in the art. Similar to the bacterial vaginosis test using luciferin or dioxetane conjugates, the test kit for a hydrogen peroxide test may have to kit components, a sample preparation buffer (e.g., 1 mL of 0.1 M $NaHCO_3$, pH 8.5) and a detection mix. The detection mix solution (e.g., 1 mL 0.1M $NaHCO_3$, pH 8.5 and 0.1 micromole of acridinium or luminol) can be used as it is or, preferably, is lyophilized for long-term storage. The detection protocol can be as follows: vaginal fluid is collected with a vaginal swab, which is rinsed in the sample preparation buffer. The resulting sample is then added to the detection mix and then subjected to detection using a luminometer. The light signal output is measured for a period of time, e.g., 10 seconds to 3 minutes, and then integrated. The total signal output is then used to determine the status of hydrogen peroxide in vaginal fluid. Again, a cutoff value can be established by testing a large number of negative clinical samples, e.g., 100 or more of negative samples. Sensitivity of the assay can be determined by testing a large number of positive clinical samples, e.g., 100 or more of positive samples. The positive samples are those from patients with vaginal infections (bacterial vaginosis or other microbial infection) that are confirmed with other well-recognized methods.

It is within the scope of the present invention that a combination of two or more tests (e.g. hydrogen peroxide test, LE activity test, proline aminopeptidase test and sialidase test described above) may be used for diagnosis of a vaginal infection. For example, a hydrogen peroxide test and sialidase test can be used in combination to diagnose a vaginal infection other than bacterial vaginosis, where low sialidase activity (below the cutoff value of the bacterial vaginosis test) and hydrogen peroxide content (below the cutoff value for samples from healthy women) in vaginal fluid may indicate the presence of non-bacterial infection such as fungal infection.

The alpha-L-fucosidase (AFU) assay is for the determination of AFU activity in patient serum or organ or other body fluid samples. AFU is a lysosomal enzyme involved in the degradation of a diverse group of naturally occurring fucoglycoconjugates. Serum AFU activity is considered a useful marker of hepatocellular carcinoma (HCC). Elevated AFU levels in serum are an early indication of HCC. Though measurement of serum fetoprotein (AFP) is a common practice for early detection of HCC, use of AFP assay alone suffers from its low specificity and sensitivity, due to the fact that not all HCC secrete AFP. AFP levels may be normal in as many as 40% of patients with early HCC and 15-20% of patients with advanced HCC. Recent studies have clearly demonstrated that measurements of both AFP and AFU can significantly increase the detection specificity and sensitivity for HCC. AFU is reported to be a more sensitive marker, especially for detecting a small tumor size of HCC. It has also been shown that abnormal AFU level exists in serum samples from patients suffering from adult leukemia or ovarian carcinoma. In addition, AFU level is also high in patients suffering from liver cirrhosis and chronic hepatitis. According to the present invention, AFU level in a sample is quantified using a synthetic substrate alpha-L-fucopyranoside-firefly luciferin conjugate, whose chemical structure is similar to FIG. 3, which depicts a conjugate between neuraminic acid and firefly luciferin. In the alpha-L-fucopyranoside-firefly luciferin conjugate, the neuraminic acid portion in FIG. 3 is replaced with alpha-L-fucopyranoside.

In a chemiluminescent AFU assay, alpha-L-fucopyranoside-firefly luciferin conjugate is cleaved by alpha-L-fucosidase in a sample to release free firefly luciferin, which can be quantified in a chemiluminescence reaction in the presence of firefly luciferase, ATP and other appropriate conditions. It can be a one-step assay or two steps assay as those described in the sialidase test for bacterial vaginosis diagnosis. The assay kit can be similar to those used for sialidase detection except the substrate is firefly luciferin-alpha-L-fucopyranoside instead. The assay protocol can be readily adopted from the bacterial vaginosis test described above by a skilled in the art.

Figure 13:
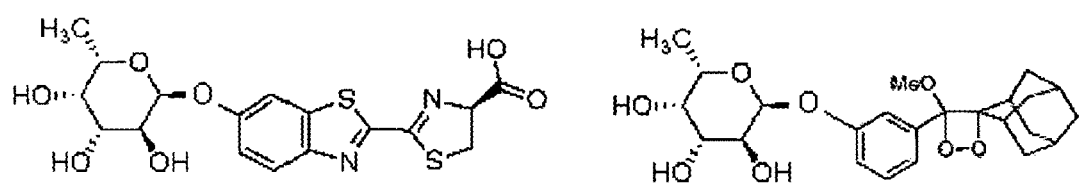
FIG. 13 shows examples of substrate for AFU activity detection.

The 1,2-dioxetane derivative-alpha-L-fucopyranoside and coelenterazine (or its derivatives)—alpha-L-fucopyranoside are also suitable substrates for chemiluminescent AFU activity detection. The structures of the dioxetane substrates can be similar to the structures depicted in FIGS. 7 and 8 except the sugar moiety in the substrates is alpha-L-fucopyranoside. Two examples suitable for AFU activity detection are shown in FIG. 13. A cutoff value for diagnosis can be established by testing a large number of negative clinical samples, e.g., 100 or more of negative samples. Sensitivity of the assay can be determined by testing a large number of positive clinical samples, e.g., 100 or more of positive samples. The positive samples are those from patients who are confirmed positive for hepatocellular carcinoma (HCC) with other well-recognized methods.

Figure 9:
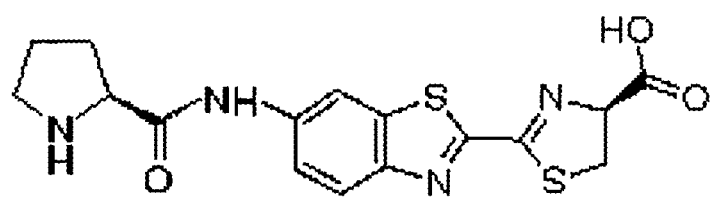
FIG. 9 shows L-prolyl-6-amino firefly luciferin.

Elevated glycylproline dipeptidyl aminopeptidase (GPDA) activity in blood and urine is associated with abnormality in liver, stomach, intestine and kidney. Elevated GPDA activity (especially the isoenzyme, GPDA-F) in serum has been identified as a reliable marker enzyme for hepatocellular carcinoma and other liver disease. The GPDA assay in the current invention is based on the enzymatic cleavage of the synthetic substrate L-glycyl-L-prolyl-6-amino firefly luciferin, whose chemical structure is similar to that of L-prolyl-6-amino firefly luciferin, which is depicted in FIG. 9. In the L-glycyl-L-prolyl-6-amino firefly luciferin conjugate, the peptide moiety is L-glycyl-L-proline. In the GPDA assay, the L-glycyl-L-prolyl-6-amino firefly luciferin conjugate is cleaved by GPDA to give rise to free luciferin, which is detected in a firefly luciferase catalyzed chemiluminescence reaction. It can be a one-step assay or two steps assay as described before. Reagent and kit formulation can be similar to those described in Examples 1 and 2 as well.

Figure 14:
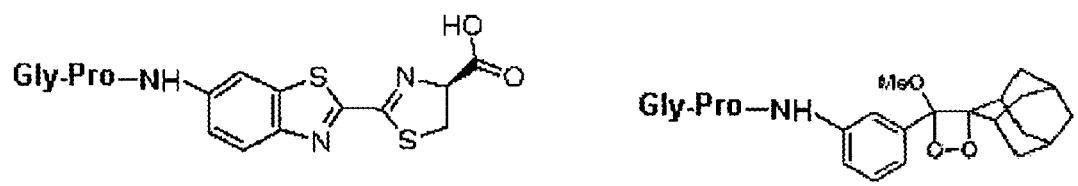
FIG. 14 shows examples of substrate for GPDA assay.

The L-glycyl-L-prolyl-1,2-dioxetane conjugates, which are similar to the substrates depicted in above proline aminopeptidase assay (L-glycyl-L-prolyl is present in the substrate instead of L-prolyl group), can also be used in chemiluminescent GPDA assay. In this assay format, the cleaved dioxetane moiety in the conjugate gives rise to the light signal that is dependent on GPDA activity in a sample. The assay protocol and reagent formulation can be readily adopted from the proline aminopeptidase assay for bacterial vaginosis detection as described before. Two examples of the substrate suitable for GPDA assay are shown in the FIG. 14. Again, a cutoff value can be established by testing a large number of negative clinical samples, e.g., 100 or more of negative samples. Sensitivity of the assay can be determined by testing a large number of positive clinical samples, e.g., 100 or more of positive samples. The positive samples are those from patients who are confirmed positive for hepatocellular carcinoma (HCC) with other well-recognized methods.

The current invention also relates to methods and reagents for the detection of organophosphorus agents, which include pesticides and nerve gas. These organophosphorus chemical agents can bind and block esterase enzymes, especially acetylcholine esterase (AChE), which is present in the blood and at the neuromuscular junctions in the peripheral and central nervous systems. AChE regulates the level of the neurotransmitter acetylcholine (ACh) by degrading it. These organophosphorus nerve agents inhibit AChE, resulting in excessive accumulation of Ach, which can fatally impair the nerve system of the individuals who are exposed to it.

Figure 15:
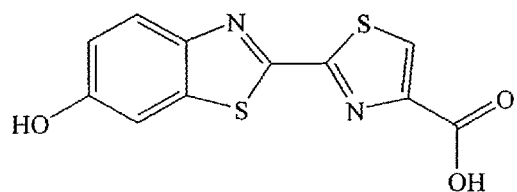
FIG. 15 shows firefly dehydroluciferin.
Figure 16:
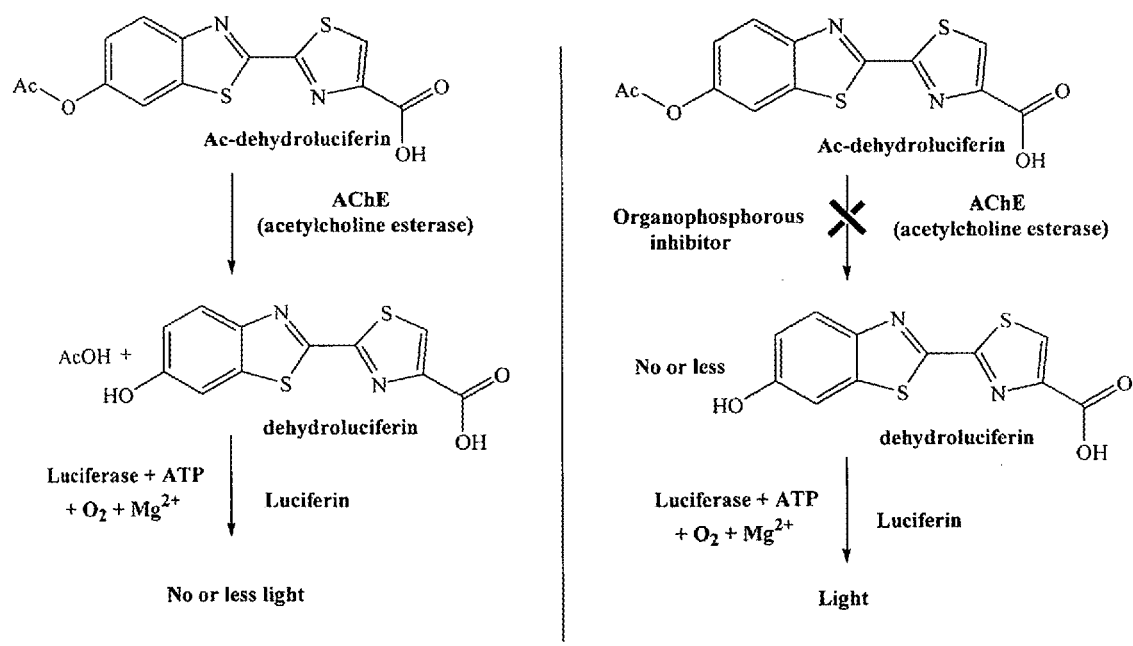
FIG. 16 provides a schematic drawing showing the luminesent acetylcholine esterase inhibition test using acetyl-firefly dehydroluciferin as substrate.

Firefly luciferin can be oxidized into a dehydrogenated form called firefly dehydroluciferin (FIG. 15), which is a potent inhibitor of firefly luciferase bioluminescence reaction with an $IC_{50}$ of 6 nM. Thus, acetyl-firefly dehydroluciferin can be used in a "positive" inhibition assay for the detection of organophosphorous agents, as depicted in FIG. 16. The reaction mix will contain four key reagents: the acetyl-dehydroluciferin, acetylcholine esterase, firefly luciferase and small amounts of firefly luciferin. In the absence of an organophosphorous agent, acetylcholine esterase hydrolyzes the substrate and releases dehydroluciferin, which inhibits firefly luciferase activity and consequently reduces the light signal. Presence of an organophosphorous agent, which inhibits the esterase, leads to a reduction of dehydroluciferin resulting in an increase of signal intensity. Thus in this assay format, the signal intensity is proportional to the concentration of the organophosphorous agent. Firefly dehydroluciferin can be synthesized according to the procedure described in the literature (E H White, F McCapra, GF Field—Journal of the American Chemical Society, 1963 v 85 p337; title: The Structure and Synthesis of Firefly Luciferin) In brief, firefly luciferin is dissolved in sodium hydroxide solution and the solution is boiled in air until thin layer chromatography (TLC) shows the absence of firefly luciferin. This process may take several hours, e.g., 8 hours. The solution is acidified with concentrated hydrochloric acid and extracted with ethyl acetate followed by silica gel column chromatography. Acetylization of firefly dehydroluciferin is performed by incubating the purified firefly dehydroluciferin with excessive amounts of acetic anhydride in pyridine at room temperature for 1 hour, followed by silica gel column purification to remove the unreacted firefly dehydroluciferin. The recovered acetyl-firefly dehydroluciferin can be further purified using a preparative HPLC to completely remove the firefly dehydroluciferin. A preferred detection mix contains 0.2 M phosphate buffer, pH 7.5, 1 mg/mL ATP, 15 mM magnesium sulfate, 4 mM calcium chloride, 0.1 nM firefly luciferin, 10 nM acetyl-firefly dehydroluciferin, 100 microgram/mL acetylcholine esterase and 1 microgram/mL firefly luciferase. 200 microliters of the reaction mix is lyophilized in a detection tube. Each detection tube is used for one sample testing. Other than the detection mix, the test kit also needs a positive control (e.g., 1 microgram/mL of organophosphurus in 1×PBS buffer) and a negative control (e.g., 1×PBS buffer). 200 microliters of sample is added to the lyophilized detection mix, incubated for 5 minutes and then placed in the detection chamber of a luminometer for detection. The light signal (RLU—relative light unit) is recorded. Background counts are determined using the negative control. This substrate and method can also be used for other esterase activity detection such as LE activity detection described above.

Figure 17:
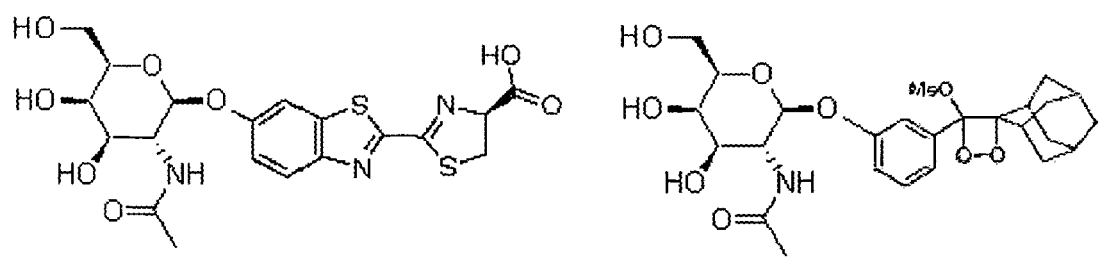
FIG. 17 provides example of chemiluminescent beta-galactosaminidase substrates.

The current invention also relates to novel chemiluminescent substrates that can be used to detect beta-galactosaminidase activity, a biomarker for *Candida albican*, which is the most common pathogen that causes yeast infection. The substrates that are suitable for chemiluminescent reaction based detection of beta-galactosaminidase are composed of two moieties, the galactosamine moiety (e.g., acetyl-galactosamine) and chemiluminescent moiety (e.g., firefly luciferin or 1,2-dioxetane), which are linked together through an appropriate chemical bond that can be cleaved by the beta-galactosaminidase. Examples of these substrates are shown in FIG. 17. In the presence of beta-galactosaminidase in a sample, the conjugate is cleaved to release free chemiluminescent moiety, firefly luciferin or 1,2-dioxetane, which becomes luminescent under appropriate conditions. The emitted light can be detected with a simple luminometer. Formulations of the reagents and test kits and detection procedures can be adopted from Examples 1 and 2 for firefly luciferin containing substrates, and Examples 5 for dioxetane-containing substrates.

The released free firefly luciferin can be quantified by measuring the chemiluminescence in the presence of firefly luciferase and ATP using the protocol described above. Other substrates such as 1,2-dioxetane derivative—N-acetyl-beta-D-galactosaminide and coelenterazine (or its derivatives)—N-acetyl-beta-D-galactosaminide (e.g. those same to the structures in FIGS. 6,7,8 except the sugar part is N-acetyl-beta-D-galactosaminide instead) are also suitable substrates for chemiluminescent beta-galactosaminidase activity detection as long as there is a moiety that enables light emitting after cleavage with the enzyme.

*Candida albicans* produces both L-proline aminopeptidase and beta-galactosaminidase enzymes whereas other yeast/bacterial species produce only one or neither of the enzymes. Therefore the above substrates can be used for *candida albicans* detection. These beta-galactosaminidase substrates can be either used alone or, in preferred embodiments, in combination with substrates for L-proline aminopeptidase (e.g. those used for proline aminopeptidase BV assay). A sample with elevated activities for both enzymes is considered positive for *Candida albicans* infection. A cutoff values for both enzymes can be established by testing a large number, e.g., 100, of negative samples. The sensitivity of the test can be evaluated by testing a large number, e.g., 100, of positive samples.

The composition of the beta-galactosaminidase test kit is similar to those used in the sialidase test except the substrate for sialidase is replaced with the substrate for beta-galactosaminidase. The amount of the substrate can be optimized experimentally for optimal detection. The pH can also be optimized experimentally for optimal detection. The composition of the L-proline aminopeptidase test kit and assay protocol can be identical to or adopted from the proline aminopeptidase test used in bacterial vaginosis detection.

Figure 18:
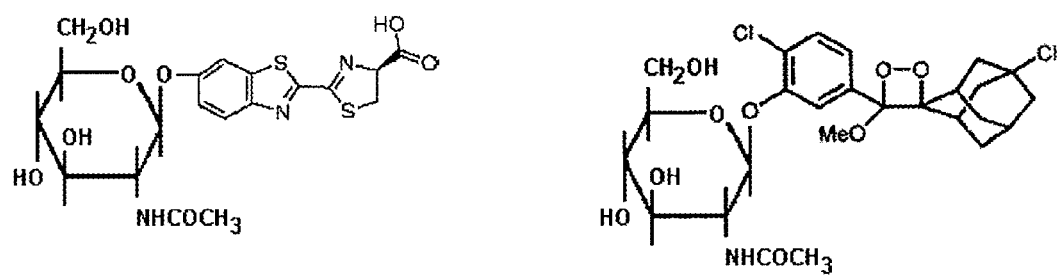
FIG. 18 provides example of chemiluminescent substrates for NAGase.

The current invention also relates to novel chemiluminescent N-acetyl-beta-D-glucosaminidase (hereinafter simply referred to as NAGase) substrates that can be used to detect NAGase activity. The NAGase can cleave the substrates and release the N-acetyl-beta-D-glucosamine and the chemiluminescent moiety such as firefly luciferin or 1,2-dioxetane derivatives, which enable luminescence reaction when they are in their free form. Examples of these substrates are shown in the FIG. 18. The free firefly luciferin can be quantified using a biochemiluminescence assay in the presence of firefly luciferase/click beetle luciferase and ATP as described above. Other substrates such as 1,2-dioxetane derivative—N-acetyl-beta-D-glucosaminide and coelenterazine (or its derivatives)—N-acetyl-beta-D-glucosaminide (such as those similar to the structures depicted in FIGS. 6,7,8 except the sugar part is N-acetyl-beta-D-glucosaminide instead) are also suitable for use in chemiluminescent NAGase activity detection as long as the released moiety can be used to produce light signal.

NAGase is one of the enzymes in lysosomes distributed in the kidney tubular epithelium in large quantities, and participates in decomposition of glucoproteins and mucopolysaccharides. It is recognized that urinary NAGase activity increases in various renal diseases such as acute renal deficiency, glomerulonephritis, etc. or in post-operative kidney. It is also recognized that in the case of diabetes the amount of NAGase increases not only in urine but also in serum. As an aid for diagnosis and monitoring of various renal diseases and also as an index in studies on renal toxicity of drugs, determination of NAGase activity has attracted much attention both in clinical fields and in animal experiments.

Substrates for use in determining NAGase activity currently used include, for example, p-nitrophenyl-N-acetyl-beta-D-glucosaminide, 4-methylumbelliferyl-N-acetyl-beta-D-glucosaminide and m-cresolsulfonephthaleinyl-N-acetyl-beta-D-glucosaminide or those described in U.S. Pat. Nos. 5,274,086 and 5,030,721. However, they are all colorimetric based test, which has low sensitivity and requires long incubation time. One objective of the present invention is to provide novel compounds overcoming the problems mentioned above for determining NAGase activity and methods of determination using these novel compounds. The compounds and methods provided in the present invention enable rapid and sensitive determination of NAGase activity.

A variety of sample sources are appropriate for use in determining the NAGase activities. Examples include culture fluids of microorganisms, plant extracts, body fluids, urine and tissues of animals and extracts thereof. If necessary, pretreatment of the sample may be performed. In addition, an oxidizing agent is added to minimize the effect of reducible substances in the sample in some applications. Appropriate buffers that can be used for the assay include, but are not limited to, phosphates, acetates, citrates, succinates, phthalates and etc. The assay can be done in either the so-called end-point assay format, in which the enzyme reaction is once discontinued to perform the determination of the enzyme activity, or the rate-assay method, which is one of the most popular methods for determining enzyme activity in many cases. It can also be done by determining the time dependent RLU or integrating the overall RLU in certain time window as described in previous applications. Alternatively, it can be done in the real time assay format, in which both reactions are performed simultaneously in a single reaction tube. In the real time assay format, the signal (relative light units) can be recorded in a time-dependent manner to measure the kinetics of the reactions or the signal over a period of time (e.g., 2 minutes) is integrated to measure an overall signal intensity.

The optimal pH for NAGase activity is 4.5-5.0. In the end point assay format, the sample can be incubated with the substrate at this optimal pH for a certain period of time (e.g., 10 minutes) followed by adjustment of pH to an optimal value for the bioluminescence reaction (e.g. pH 7.8 for firefly luciferase) or for chemiluminescence (pH 10.5 for dioxetane type substrate). In a specific example, the dioxetane-containing substrate is dissolved in 50 mM citrate buffer (pH=5.0) at an optimal concentration that is determined experimentally. 1 mL of the substrate solution is mixed with 25 microliters of a sample solution. The mixture is incubated at 25 degree C. for 5 minutes, followed by adjustment of the pH value to 10.5 using 0.2 M NaOH solution. The light signal is measured using a luminometer. A standard curve is established by testing a number of samples containing varying concentrations of NAGase activities. The NAGase activity in the sample solution is then determined by comparing the RLU from the sample with the standard curve.

Figure 19:
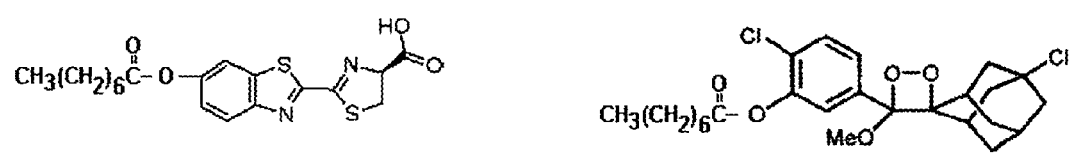
FIG. 19 provides example of chemiluminescent substrates for *salmonella* esterase.

The *Salmonella* esterase catalyzes the hydrolysis of a variety of C6 to C16 fatty acid esters but does not hydrolyze peptide bonds. Presence of this esterase activity is indicative of *Salmonella* contamination in a sample. The current invention also relates to novel chemiluminescent C6 to C16 fatty acid ester esterase substrates that can be used to detect *Salmonella*. The *Salmonella* esterase can cleave the substrates and release the chemiluminescent moiety such as firefly luciferin or 1,2-dioxetane derivatives, which can luminesce once cleaved from their conjugates. The substrates useful for the current invention are firefly luciferin fatty acid ester (C6 to C16 fatty acid) or 1,2-dioxetane fatty acid ester (C6 to C16 fatty acid). The —COOH group of the fatty acid are coupled with the 6-OH group of the firefly luciferin or the —OH on the 1,2-dioxetane to generate an ester bond. These esters are similar to the structures in FIGS. 6,7,8 and sialidase substrates in the BV test except that the sugar part is replaced by the fatty acid group, e.g. an caprylyl group, which form an ester bond. One preferred fatty acid is caprylic acid. Examples of these substrates are shown in the FIG. 19. In one embodiment, the dioxetane-containing substrate is dissolved in 1×PBS buffer (pH=7.5) at an optimal concentration that is determined experimentally. 0.5 mL of the substrate solution is mixed with 200 microliters of a sample solution. The mixture is incubated at 25 degree C. for 5 minutes, followed by adjustment of the pH value to 10.5 using 0.2 M NaOH solution. The light signal is measured using a luminometer. A cutoff value can be established by testing a large number of negative samples that contain no *Salmonella* esterase-activities. Higher light signal indicate the presence of higher amount of *Salmonella* contamination.

Figure 20:
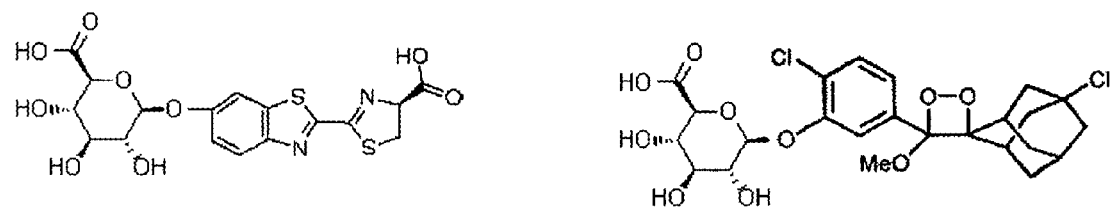
FIG. 20 provides example of chemiluminescent substrates for beta-glucuronidase.

The current invention also relates to novel chemiluminescent beta-glucuronidase substrates that can be used to detect beta-glucuronidase activity. The beta-glucuronidase cleaves the substrates and release the beta-D-glucuronic acid and the chemiluminescent moiety such as firefly luciferin or 1,2-dioxetane derivatives, which can luminesce once cleaved from their conjugates and under appropriate conditions. Examples of these substrates are shown in FIG. 20. The released free firefly luciferin can be quantified in a biochemiluminescence reaction that uses firefly luciferase and ATP. Protocols for this type of biochemiluminescent assays are described above (e.g., Examples 1 and 2). Other substrates such as 1,2-dioxetane derivative-beta-D-glucuronide and coelenterazine (or its derivatives)—beta-D-glucuronide (e.g. those similar to the structures in FIGS. 6,7,8 except that the sugar moiety is beta-D-glucuronide) are also suitable for use in detection of beta-glucuronidase activity in a chemiluminescent assay as long as the released chemiluminescent moiety can be used to produce light signal. Quantitative detection of beta-glucuronidase activity has many applications. For example, many carcinoma patients show elevated beta-glucuronidase (beta-G) activity. Elevated activity of beta-G in blood serum can be detected in patients with early hepatic carcinoma; Elevated activity of beta-G in blood serum and CSF in patients with cerebral tumor can also be detected. In addition, some microorganism such as *E. coli* also has elevated β-glucuronidase activity, which can be used for detection of these microorganisms in a sample, e.g., *E. coli* contamination in food. The general protocols of using these substrates for detection of beta-glucuronidase activity are similar to other enzyme detection described above and can be readily adopted by a skilled in the art.

Figure 21:
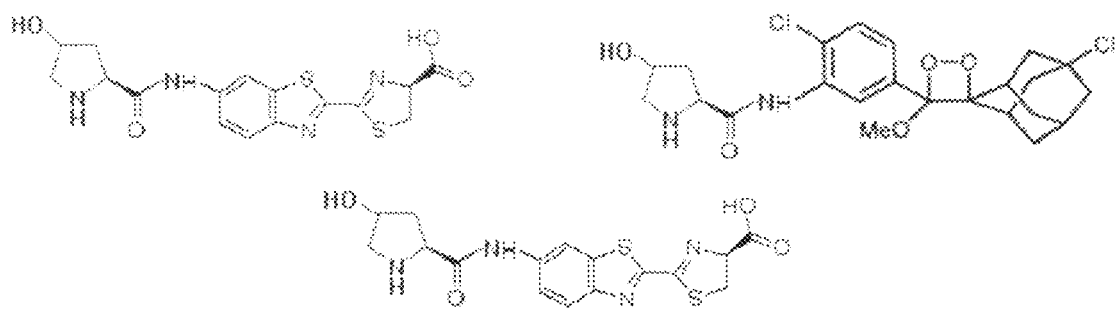
FIG. 21 provides example of chemiluminescent hydroxyproline aminopeptidase substrates.

The current invention also relates to novel chemiluminescent hydroxyproline aminopeptidase substrates that can be used to detect hydroxyproline aminopeptidase, which can cleave the substrates and release the hydroxyproline and the chemiluminescent moiety such as firefly luciferin or 1,2-dioxetane derivatives, which enables luminescence in their free form. Examples of these substrates are shown in FIG. 21. The free firefly luciferin can be quantified in a biochemiluminescence that uses firefly luciferase and ATP. Appropriate protocols are similar to other enzyme detection described above and can be readily adopted by a skilled in the art. Other substrates such as hydroxyproline-1,2-dioxetane derivative and hydroxyproline-coelenterazine (or its derivatives) (similar to the substrates used in proline aminopeptidase assay described above but the proline moiety is replaced by a hydroxyprolyl group) are also suitable for detection of hydroxyproline aminopeptidase activity in a chemiluminescent assay as long as the released chemiluminescent moiety can enable the production of light signal. Preferably the —OH on the proline is a trans-hydroxy group.

In one example, during the assay, the aminopeptidase cleaves the synthetic substrate and releases the free 6-amino firefly luciferin, which can be quantified in a biochemiluminescent assay that uses firefly luciferase and ATP. In yet another example, the 1,2-dioxetane substrate is used for chemiluminescent hydroxyproline aminopeptidase activity detection. The assay protocol can be adopted from that which is described in the proline aminopeptidase assay.

Hydroxyproline aminopeptidase assay can also be used to detect *Neisseria gonorrhoeae*. For example, the vaginal samples from *neisseria gonorrhoeae* patients show high level of hydroxyproline aminopeptidase activity. Therefore, the substrates described in the current invention can be used for diagnosis of *neisseria gonorrhoeae* infection.

The current invention discloses a series of chemiluminescent substrates for different enzymes. These substrates have the following formulas:

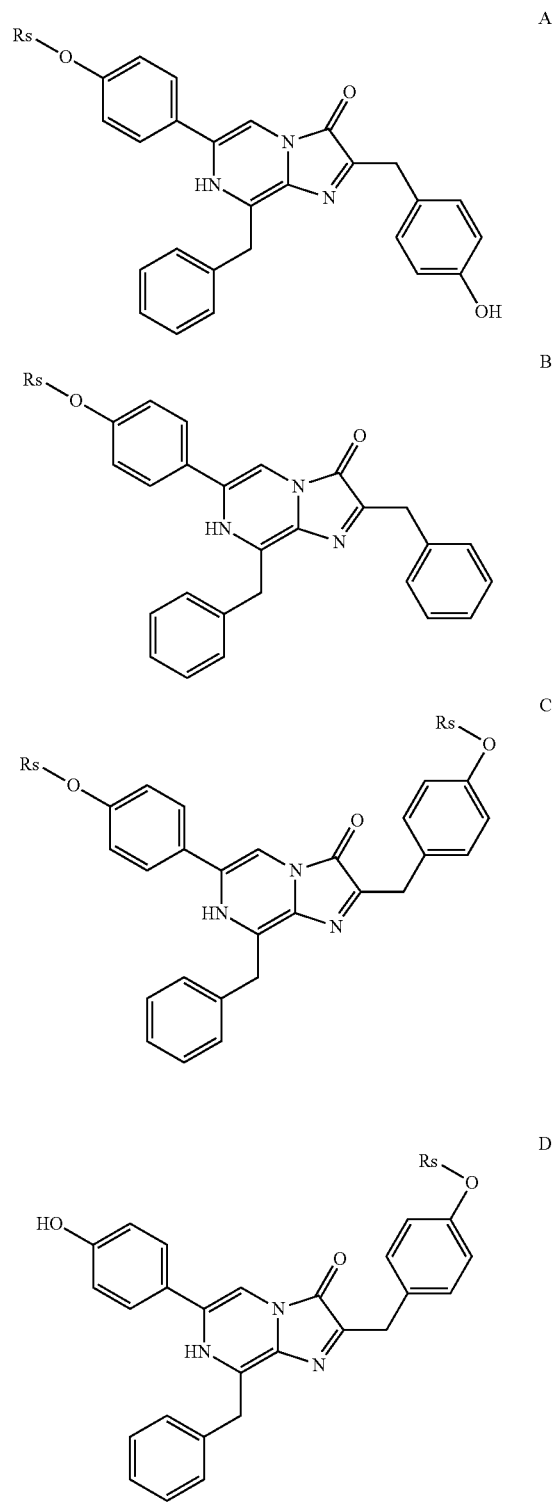

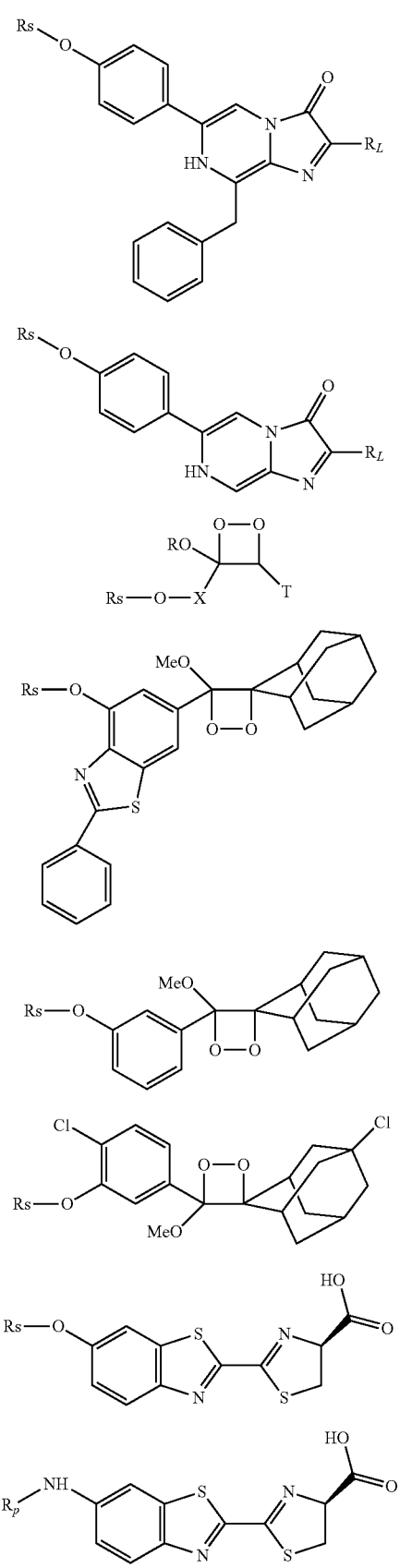

Wherein:

$R_L$ is H or alkyl group of 1-20 carbon atoms such as methyl group; T is a substituted or unsubstituted polycycloalkyl group bonded to the 4-membered ring portion of the dioxetane by a Spiro linkage; X is an aryl or heteroaryl moiety of 6-30 carbon atoms which induces chemiluminescent decomposition of the 1,2-dioxetane upon enzymatic cleavage of moiety Rs; R is an alkyl, aryl, aralkyl or cycloalkyl of 1-20 carbon atoms. Examples of R, X and T are described in U.S. Pat. No. 6,555,698. The specific substitution group in the substrate for the corresponding enzyme is shown in the table below:

| Substitution symbol | Substitution group | Substrate for enzyme |
|---|---|---|
| Rs | -alpha-L-arabinopyranoside | alpha-L-Arabinosidase |
| Rs | -beta-D-cellobioside | beta-Cellobiosidase |
| Rs | -alpha-L-fucopyranoside (Described in the above AFU assay) | alpha-L-Fucosidase |
| Rs | -beta-D-fucopyranoside | beta-D-fucosidase |
| Rs | -beta-L-fucopyranoside | beta-L-Fucosidase |
| Rs | -N-acetyl-alpha-D-galactosaminide | alpha-Galactosaminidase |
| Rs | -N-acetyl-beta-D-galactosaminide (Described in the above *Candida albicans* test) | beta-Galactosaminidase |
| Rs | -alpha-D-galactopyranoside | alpha-Galactosidase |
| Rs | -beta-D-galactopyranoside | beta-Galactosidase |
| Rs | -N-acetyl-alpha-D-glucosaminide | alpha-Glucosaminidase |
| Rs | -N-acetyl-beta-D-glucosaminide (Described in the above NAGase test) | beta-Glucosaminidase |
| Rs | -alpha-D-glucopyranoside | alpha-Glucosidase |
| Rs | -beta-D-glucopyranoside | beta-Glucosidase |
| Rs | -beta-D-glucuronic acid (Described in the above beta-Glucuronidase test) | beta-Glucuronidase |
| Rs | -beta-D-lactopyranoside | beta-Lactosidase |
| Rs | -beta-D-maltopyranoside | alpha-Maltosidase |
| Rs | -alpha-D-mannopyranoside | alpha-Mannosidase |
| Rs | -beta-D-mannopyranoside | beta-Mannosidase |
| Rs | -beta-D-xylopyranoside | beta-Xylosidase |

As described above, the general principle for detecting these enzyme activities using these listed chemiluminescent substrates involve two steps. The first step is the enzyme cleaving the substrate and releasing the chemiluminescent molecule. The second step is the chemiluminescent molecule emitting light under suitable condition (e.g. high pH or catalyzed by luciferase). In the first step, the ingredients in the reagent mix and the buffer need to be formulated to allow the target enzyme cleaving the substrate (e.g. suitable pH and the presence of certain ion). These formulations are well known for the skilled in the art. Sometimes the condition suitable for the first step is also suitable for the chemiluminescent molecule emitting light. Therefore the two steps can be combined. Sometimes the condition suitable for the first step is not suitable for the chemiluminescent molecule emitting light, therefore additional reagent and/or buffer need to be added after the cleavage of the substrate to satisfy the condition for the chemiluminescent reaction.

The present invention further provides methods and compositions for firefly luciferase (or other luciferase utilizing firefly luciferin and ATP, e.g. click beetle luciferase) based homogeneous enzyme channeling luminescent assays for analyte detection. Analyte is molecule or composition to be measured, which may be a ligand, small molecule, large molecule, protein, enzyme, peptide, nucleic acid and etc.

The invention utilizes the enzyme channeling effect to detect the analyte. Enzyme channeling effect utilizes two enzymes, which are related by the product of one being the substrate of the other. Therefore, when the two enzymes are close to each other a greater turnover would be expected of the product of the first enzyme in the series by the second enzyme in the series. Therefore, there will be at least one compound (substrate) as part of a signal producing system which is capable of being modified by a first enzyme to produce a product which will be modified by a second enzyme to produce a second product which, directly or indirectly provides a detectable signal.

Current invention utilizes the enzyme channeling phenomenon to detect the analyte. An enzyme channeling system is composed of two enzymes, in which the first enzyme acts on a substrate and produces a product that is the substrate of the second enzyme. Enzymatic action of the second enzyme produces a signal such as light signal that can be detected directly or indirectly.

It is known to the skilled in the art that in the enzyme channeling system as described above, physical proximity of the two enzymes affects the signal output. The closer the two enzymes are, the stronger signal there is. This phenomenon can be used to detect direct or indirect interaction or binding of the two enzymes in the system. The interaction may be a receptor-ligand interaction or its variations, an antibody-antigen interaction or its variations, a nucleic acid complementation based interaction or its variations, an aptamer based interaction or its variations, or the likes, including those that have yet been discovered. A skilled in the art is able to devise a suitable interaction for detecting a specific analyte.

Figure 22:
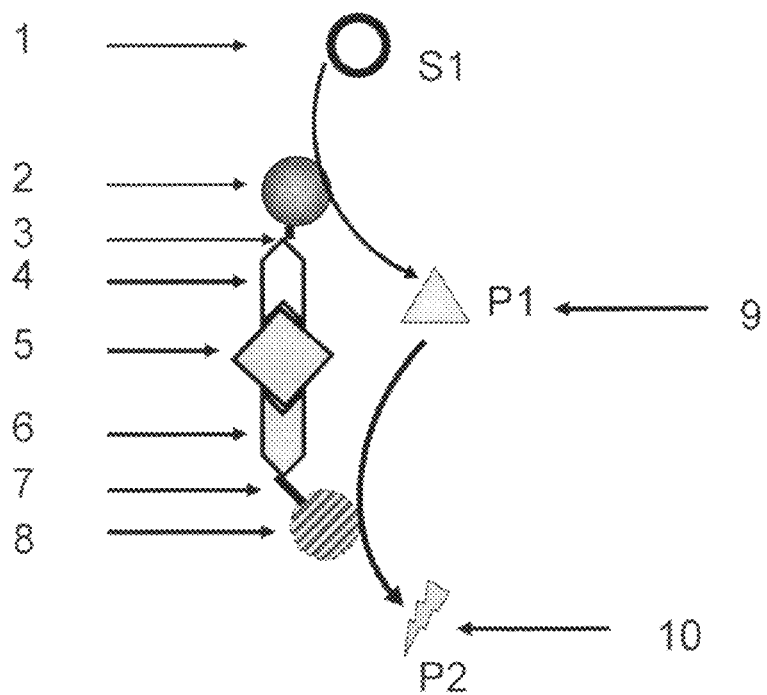
FIG. 22 provides an example of enzyme channeling based detection system.

One example of the enzyme channeling based detection system is best understood by referring the example depicted in the FIG. 22. The first enzyme 2 is coupled to the first receptor 4 through a chemical bond 3 whereas the second enzyme 8 is coupled to the second receptor 6 via a chemical bond 7. In the presence of a ligand/analyte 5 that has distinct binding sites for the first and second receptors, the first and second enzymes are brought together through the interaction of receptors and ligand, thus forming an enzyme channel. The action of the first enzyme 2 on the first substrate 1 (S1) produces the first product 9 (P1), which is the substrate for the second enzyme 8. The second enzyme 8 converts the first product 9 (P1) to a detectable product 10 (P2). In this system, presence of an analyte results in higher signal. Thus, increased signal intensity indicates the presence of a specific analyte.

It is understood that the enzyme channels or the construction of these channels may vary from what is depicted in FIG. 22. For example, the first enzyme 2 and first receptor 4 can be conjugated to solid phase support such as micro- or nanoparticle. Similarly, the second enzyme 8 and second receptor 6 can also be conjugated to solid phase support such as micro- or nanoparticle. Because of the binding of a single analyte (ligand 5) can result in indirect interaction of multiple enzyme molecules, amplification can be achieved.

A number of techniques known to the skilled in the art can be used to couple the enzymes to the ligands or receptor or the likes. For example, techniques are available for directly coupling a specific antibody with an enzyme such as alkaline phosphatase. The coupling can be done via a carrier system as well, e.g. a linker molecule, a polymer, a protein, a solid phase matrix such as a microsphere or nanoshpere. One example is that both the second ligand/receptor and firefly luciferase are coupled with a biotin group. The biotinylated ligand and firefly luciferase are then used to coat an avidin coated microparticle or nanoparticle, resulting a microparticle or nanoparticle coated with both the ligand/receptor and luciferase. The coupling/labeling techniques and different labeling formats are well known to the skilled in the art and can be found in varieties of publications.

In the enzyme channeling system described above, background signal may still be produced even in the absence of an analyte (ligand 5), albeit, with weaker signal. However, a number of methods can be used to reduce this background signal. For example, a monoclonal antibody that specifically binds to the first product 9 (P1) can be used to sequester the first product (P1). This sequestering antibody competes with the second enzyme 8 for the first product 9.

However, presence of an enzyme channel, i.e., presence of ligand 5 (the analyte) favors the first product to be channeled to the second enzyme. Alternatively, a degrading enzyme that competes with the second enzyme 8 for the first product 9 but does not generate detectable signal can also be used to reduce the background.

It is understood that conditions need to be optimized to achieve the best signal to noise ratio for an assay. For example, the optimal concentrations of the enzyme conjugates, sequestering antibody, and substrates etc may be experimentally determined using methods known to the skilled in the art.

The current invention is based on the use of firefly luciferin luminescent systems. In some embodiments, the two enzymes utilized for enzyme channeling are firefly luciferin producing enzyme and firefly luciferase or other luciferase utilizing firefly luciferin such as click beetle luciferase. In other embodiments, those two enzyme utilized are ATP producing enzyme and firefly luciferase or other luciferase utilizing ATP such as click beetle luciferase.

When firefly luciferin producing enzyme is used, substrate that can be used by the firefly luciferin-producing enzyme to produce firefly luciferin is also needed in the assay. Examples of these substrate-firefly luciferin producing enzyme are listed below: firefly luciferin methyl ester and carboxylic esterase, firefly luciferin O-sulfate and arylsulfatase, firefly luciferin O-phosphate and alkaline phosphatase, firefly luciferyl-L-N alpha-arginine or firefly luciferyl-L-phenylalanine and carboxypeptidases A, B and N, firefly-luciferin-O-beta-galactoside and beta-galactosidase, other examples can be found in U.S. Pat. No. 5,098,828, US Patent 20070015790. The enzyme and its corresponding substrate described in the early part of this invention such as N-acetylneuraminic acid-firefly luciferin conjugate and sialidase, L-prolyl-6-amino firefly luciferin and proline aminopeptidase are also suitable for this method. The general requirement for these substrate-enzyme pair is that the enzyme should be able to convert the corresponding substrate and generate firefly luciferin or its analogue that can produce light signal by firefly luciferase while the unconverted substrate does not luminesce by luciferase or only luminesce very weakly. In certain embodiments, a luciferin sequestering antibody is used in the system to reduce the background.

When ATP producing enzyme is used, free firefly luciferin or its analogue (e.g. firefly 6-amino luciferin) that can luminesce by firefly luciferase or other luciferase utilizing firefly luciferin such as click beetle luciferase is needed in the system instead of the substrate that can be converted to firefly luciferin such as those described above. In this system, an ATP producing enzyme is used as the first enzyme to produce ATP that enables luciferase-based chemiluminescence reaction. In this enzyme channeling system, free firefly luciferin or its analogue (e.g. firefly 6-amino luciferin) is still used in the reaction. Any enzyme that can produce ATP can be used in the invention such as nucleoside diphosphate kinase, phosphoglycerate kinase, pyruvate kinase, sulfurylase, acetate kinase and the corresponding substrates that can produce ATP such as ADP are also need to be provided. In another word, any enzyme that can produce ATP can be used as the first enzyme in the present invention. Examples of these enzymes include, but are not limited to, phosphoglycerate kinase and pyruvate kinase. Appropriate substrates and conditions need to be provided in order for the enzyme to produce ATP. For example, 1,3-biphosphoglycerate and ADP must be present in order for phosphoglycerate kinase to convert ADP to ATP. Similarly, phosphoenolpyruvate and ADP must be provided in order for pyiuvate kinase to produce ATP, which is subsequently used in the firefly luciferase-catalyzed chemiluminescent reaction. In another example, sulfate adenylyltransferase (ATPS) is used, which converts APS (adenosine 5'-phosphosulfate) to ATP in the presence of PPi, for generating ATP.

In order to detect a specific analyte, two affinity ligands need to be provided, the first ligand can bind with one part/area of the analyte and the second ligand can bind with another part/area of the analyte and therefore can form a sandwich type structure similar to those in the classical ELISA type assay. Suitable ligands include antibody, nucleic acid, small molecule, protein, aptamer, receptor and etc. These types of ligands-analyte complex are very common in modern assay and are well known to the skilled in the art. In the current invention, the first ligand (or ligands, e.g. multiple copies of ligand having same binding mode) is coupled (sometimes called labeled) with firefly luciferin producing enzyme/enzymes (or ATP producing enzyme/enzymes) and the second ligand (or ligands) is coupled with firefly luciferase/luciferases. The coupling can be done via a carrier system, e.g. a linker molecule, a polymer, a protein, a solid phase matrix such as a microsphere. One example is that both the first ligand and firefly luciferase have a biotin group and upon being mixed with an avidin coated solid phase support such as micro particle the first ligand and firefly luciferase will be immobilized on the solid phase support generating the ligand labeled firefly luciferase. In this case, it is possible that each particle carry multiple copies of the first ligand molecule and firefly luciferase. The coupling/labeling/coating techniques and different labeling formats are well known to the skilled in the art and can be easily found in varieties of publications.

For example, in an assay to detect a specific protein A, two monoclonal antibodies against different regions of protein A is used. The first antibody is labeled with phosphatase, the second one is co immobilized together with firefly luciferase on the solid phase support (e.g. Sepharose beads). Alternatively, the second antibody can be directly labeled with firefly luciferase. When these is protein A in the sample, upon incubation, a sandwich structure will form which can be described as first antibody—phosphatase-protein A—second antibody-firefly luciferase and therefore the firefly luciferase is very close to the phosphatase. The corresponding substrate firefly luciferin O-phosphate can be added before or during or after the incubation. The phosphatase will cleave the phosphate group and release the free firefly luciferin and the released firefly luciferin will be consumed preferably by the nearby firefly luciferase and generate light signal which can be in turn measured with suitable means such as a luminometer. The assay solution is formulated to contain all the reagents and condition such as ATP and suitable pH necessary for the activity for both enzymes. No free firefly luciferin is added. This assay can be performed directly in the sample solution. The protocol is very simple and no separation step is required to remove the excess unbound labeled antibodies. The assay protocol is limited to the addition of sample, substrate, and other reagents. The light signal generated is related to the amount of sandwich structure formed and therefore related to the amount of analyte in the assay. Because the unbound phosphatase will also produce free firefly luciferin that can generate light signal when it is consumed by bound or unbound firefly luciferase and therefore may cause background luminescence signal, an antibody that can specifically bind with free firefly luciferin and block its ability to luminesce can be added to the assay, however, this antibody should not interfere the substrate being converted to free firefly luciferin by the firefly luciferin producing enzyme. The amount of the antibody added can be determined experimentally to reach the optimal signal/noise ratio. This antibody works as a scavenger to neutralize the background producing firefly luciferin since the firefly luciferin generated within the sandwich complex will less likely been blocked by the antibody.

When ATP producing enzyme is used for the above assay, no firefly luciferin producing enzyme (e.g. phosphatase) labeled antibody is required. The two antibodies would be labeled with ATP producing enzyme and firefly luciferase respectively. Free firefly luciferin is added either before or during or after the sandwich structure formed (e.g. the incubation). Substrate for ATP producing enzyme such as ADP is added instead of the firefly luciferin O-phosphate either before or during or after the incubation. The formulation and protocol need to provide condition for both ATP producing enzyme and firefly luciferase's activity. In order to decrease the background noise, instead of firefly luciferin specific antibody, an ATP eliminating enzyme such as ATP hydrolysase can be added to degrade the ATP generated not within the sandwich complex, which may cause background light signal. In this assay, no free ATP needs to be added. The light generated solely depends on the ATP produced by the ATP producing enzyme.

There are many scientific publications and patents described ATP producing enzyme suitable for the current invention. For example, U.S. Pat. No. 5,246,834, which is cited here solely for reference, described an EIA method using an ATP-generating enzyme as a labeling enzyme. The ATP generated by the enzyme is detected in a bioluminescence assay that uses firefly luciferase. The emitted light signal is proportional to the amounts of the analyte in the sample. In this patent, acetate kinase is a preferred enzyme for generating ATP. The enzyme, reagent and protocol used for ATP generating in U.S. Pat. No. 5,246,834 can be readily adopted by the skilled in the art for the homogenous assay described in the present invention.

There are also many scientific publications and patents described ATP eliminating enzyme suitable for the current invention. For example, U.S. Pat. No. 5,891,702, which is cited here solely for reference, described a process for eliminating effectively ATP in a sample, using adenosine phosphate deaminase alone or in combination with at least one enzyme selected from the group consisting of apyrase, alkaline phosphatase, acid phosphatase, glycerokinase, hexokinase and adenosine triphosphatase. The enzymes, reagents and protocol used for ATP eliminating in U.S. Pat. No. 5,891,702 can be readily adopted by the skilled in the art for the homogenous assay described in the current invention.

The assay for other analyte such as small molecule and nucleic acid can also be performed based on the above principle. The reagents and protocol can be easily adopted form the above case by a skilled in the art. Alternatively, competitive binding assays can also be used based on the same mechanism described above. The principle and protocol of the competitive assay is well known for the skilled in the art. For example, in an assay to detect a specific protein A or small molecule A, one monoclonal antibody against A is used. The antibody is labeled with phosphatase and A is labeled with firefly luciferase (or A is labeled with phosphatase and the antibody is labeled with firefly luciferase). The assay solution contains preformed sandwich structure antibody—phosphatase-A-firefly luciferase and therefore the firefly luciferase is very close to the phosphatase. After it is incubated with the sample, if there is A in the sample, some of the above antibody-antigen complex will disassociate proportional to the amount of free A in the sample because antibody—phosphatase-A will form competitively. The corresponding substrate firefly luciferin O-phosphate can be added before or during or after the incubation. The phosphatase will cleave the phosphate group and release the free firefly luciferin and the released firefly luciferin will be consumed preferably by the nearby firefly luciferase and generate light signal which can be in turn measured with suitable means such as a luminometer. Now the intensity of light produced is proportional to the amount of antibody—phosphatase-A—firefly luciferase complex which in turn is determined by the amount of free A in the sample. The more A in the sample, the lower the light produced.

EXAMPLE 1

Detecting of Influenza Neruaminidase

In this example, the influenza test kit contains two key components: conjugate mix and detection mix.
Reagent Compositions
Conjugate Mix (Lyophilization is Preferred)

| MES, pH 6.5 | 32.5 mM |
|---|---|
| CaCl$_2$ | 4 mM |
| BSA | 1 mg/mL |
| Triton X-100 | 0.5% |
| Mannitol | 4% |
| Sucrose | 1% |
| Conjugate | 100 µg/mL |

Detection Mix (Lyophilization is Preferred)

| Trizma, pH 7.8 | 100 mM |
|---|---|
| MgSO$_4$ | 15 mM |
| BSA | 1 mg/mL |
| ATP, Na Salt | 12 mM |
| NP$_{40}$ or Equivalent | 0.1% |
| DTT | 10 mM |
| Co-enzyme A | 1 mM |
| EDTA, Na Salt | 2 mM |
| Mannitol | 4% |
| Sucrose | 1% |
| Firefly Luciferase | 20 µg/mL |

Assay Protocol
In this example, the influenza virus detection assay comprises essentially two steps: 1) cleavage of sialic acid-firefly luciferin conjugate with influenza neuraminidase, and 2) detection of released firefly luciferin. Specifically one can use the following basic protocol:
1. Mix the sample containing flu virus with 100 µL conjugate solution, which will lyse the virus because of the presence of Triton X-100.
2. Incubate at room temperature for 10-15 minutes.
3. Transfer the solution to 100 µL firefly luciferase reaction solution pre-loaded into a detection tube, or a lyophilized detection mix in a detection tube.
4. Place the detection tube into a luminomter and record the light signal (relative light unit) for an appropriate period of time (e.g., 30 seconds).
Note that firefly luciferase mediated biochemiluminescence reaction is of a glow light type, which stably emits light for at least 5 minutes. Therefore, there is no need to use a luminometer with an automated injector. Click beetle luciferase can also be used instead of the firefly luciferase.

EXAMPLE 2

Detection of Influenza Viral Neuraminidase in a One Step Real Time Detection Format In brief, influenza virus collected in the throat nasal swab is lysed in a virus lysis buffer (PBS+1% Triton×100). A portion of the lysis buffer (200 µL) is then added to a pre-mix containing all necessary reagents, followed by incubation for 10-15 minutes at room temperature. Presence of influenza virus, hence the viral neuraminidase, results in the cleavage of a substrate, which enables the generation of visible light signal that is detected with a portable luminometer. Click beetle luciferase can also be used instead of the firefly luciferase.
Detection Mix (Lyophilized Form Preferred)

| Imidazole, pH 7.0-7.2 | 50 mM |
|---|---|
| BSA | 1 mg/mL |
| ATP, Na Salt | 12 mM |
| DTT | 10 mM |
| Co-enzyme A | 1 mM or 10 mg/mL |
| MgSO4 | 15 mM |
| CaCl2 | 4 mM |
| Mannitol | 4% |
| Sucrose | 1% |
| Sodium Azide | 0.05% |
| Firefly Luciferase | 20 µg/mL |
| Substrate | 20 µg/mL (or as determined by QC test) |

Assay Protocol
Step 1—Sample Preparation:
Place the throat swab into the Virus Lysis Buffer tube,
Roll the swab at least three times while against the bottom and side of the tube,
Wring out the swab by squeezing the tube wall against the swab and carefully pulling out the swab from the tube.
Discard the swab in a biohazard container.
Step 2—Transfer 200 µL of the sample prepared in Step 1 to a Detection Mix test tube. Cap the vial. Gently swirl the tube until all of the lyophilized powder is wet. Particulate materials may initially be present in the mix, which does not interfere with the detection.
Step 3—Incubate at room temperature (20-30° C.) for 15 minutes.
Step 4—Place the test tube in the luminometer and press the start button. Record and print the test results.

EXAMPLE 3

Use of Antibodies for Inhibiting Non-Specific Neuraminidase Activity in an Influenza Viral Neuraminidase Assay The commonly used clinical samples for influenza detection are throat and nasal swabs. Some bacterial species that are found in nasal or oral can also secret neuraminidase. These bacterial species include *Streptococcus pneumoniae* and *Actinomyces viscosus*. In this example, monoclonal or polyclonal antibodies specific for the neuraminidases for these bacterial species are added to the conjugate mix in Example 1 or the lysis buffer in Example 2. Bacterial neuraminidase in the sample, if any, is blocked by the antibodies thereby reducing the background due to non-specific bacterial neuraminidase.

EXAMPLE 4

Diagnosis of Bacterial Vaginosis Using an N-Acetylneuraminic Acid-Firefly Luciferin as the Chemiluminescent Substrate In this example, an N-acetylneuraminic acid-firefly luciferin conjugate is used as the chemiluminescent substrate for detection of bacterial vaginosis. A detection mix described in Example 2 can be used for this purpose. However, it is understood that the detection mix can be optimized for bacterial vaginosis detection since sialidase activity in a vaginal sample may be considerably higher than that for a sample for influenza detection.

The detection mix solution described in Example 2 is used to demonstrate the detection of bacterial vaginosis. The Osom BV blue positive control and negative control (from Genezyme Diagnostics), which contain different levels of bacterial sialidase used for bacterial vaginosis diagnosis, are used to demonstrate the use of the detection mix for bacterial vaginosis detection. 40 microliters of the control sample was mixed with 50 microliters of detection mix described in Example 2 in room temperature and immediately placed in a luminometer. The chemiluminescence started instantly for the positive control. The chemiluminescence signal (relative light unit) from the positive control was 300 times higher than the negative sample, demonstrating that the detection mix could well separate the positive samples from the negative ones. The assay is highly sensitive and quantitative. In addition, the assay requires no incubation, which greatly reduces the assay time.

For detection that uses a patient sample, i.e., vaginal swab, the vaginal swab can be first rinsed in a sample buffer, e.g., 1 mL of 1×PBS buffer, which or a portion of which is mixed with the detection mix in solution form or, preferably, in lyophilized form in a test tube. The test tube is placed in a luminometer for detection. It is understood that a cutoff value for the diagnosis in terms of light signal intensity (RLU) needs to be established by testing a large number of negative and positive samples, preferably more than 100 positive samples and 100 negative samples.

EXAMPLE 5

Diagnosis of Bacterial Vaginosis Using an N-Acetylneuraminic Acid-Dioxetane as the Chemiluminescent Substrate In addition to the N-acetylneuraminic acid-firefly luciferin conjugates described in Example 4, other chemiluminescent conjugates can also be used for bacterial vaginosis detection. In this example, 3 mg of a dioxetane conjugate depicted in FIG. 7 or 8 is dissolved in 1 mL of 0.5 M sodium acetate buffer (pH 7.6). 10 uL of this detection solution is mixed in a test tube with 200 microliters of vaginal fluid sample, which is prepared by rinsing a vaginal swab in 1 mL 0.1 M PBS buffer (pH 7.6). The test tube is placed in a luminometer, which reads and integrates the signal for 10 seconds to 3 minutes. Again, a cutoff value in terms of light signal intensity (RLU) needs to be established by testing a large number of negative and positive samples, preferably more than 100 positive samples and 100 negative samples.

The dioxetane conjugate can be lyophilized for long-term storage, in which case the vaginal fluid sample can be directly added to the lyophilized dioxetane conjugate mix followed by detection using a luminometer. The test can also follow the protocol described in Analytical Biochemistry 280, 291-300 (2000) in a two steps manner: first, the substrate is incubated with the sample for 5-10 minutes at low pH (e.g. pH 5~6), then mixed with the high pH triggering reagent (e,g, by adding 100 uL of the Sapphire enhancer, pH10.5) to initiate the chemiluminescence for reading. The one step method is preferred because it simplifies the assay. Because at low pH, the dioxetane has low chemiluminescence, the preferred pH for the one step assay is between 7~8.5.

EXAMPLE 6

Diagnosis of *Candida Albicans* Infection Using Chemiluminescent Substrates

In this example, 1,2 dioxetane—N-acetyl-beta-D-galactosaminide substrate is used for detection of the beta-galactosaminidase activity whereas L-propyl-1,2-dioxetane derivative substrate is used for detection of aminopeptidase activity.

The clinical sample (e.g. vaginal fluids) is suspended in 500 microliters of 0.1 M PBS buffer (pH 7.0). 250 microliters of this sample is mixed with 10 microliters of beta-galactosaminidase detection mix (3 mg of dioxetane substrate in 1 mL of 0.5 M sodium acetate buffer at a pH of about 6.5) in a vial, incubated for 5-10 minutes at 30 degree C., mixed with 100 microliters of trigger reagent (Sapphire enhancer, pH 10.5) and measured for the light signal using a luminometer. Interpretation of the test result (positive or negative for beta-galactosaminidase) is based on the established cutoff value.

The remaining 250 microliters of sample is mixed with 10 microliters of L-proline aminopeptidase detection mix (3 mg of dioxetane substrate dissolved in 1 mL of 0.5 M sodium acetate buffer at a pH of about 8.0) in another vial, incubated for 5-10 minutes 30 degree C., mixed with 100 microliters of trigger reagent (Sapphire enhancer, pH10.5) and then measured for the light signal using a luminometer. Interpretation of the test result (positive or negative for aminopeptidase) is based on the established cutoff value. Infection with *Candida albicans* is indicated when both the activities for both enzymes exceed the cutoff values.

EXAMPLE 7

Detection of an Antigen Using a Firefly Luciferase Based Enzyme Channeling System In this example, the enzyme channeling based assay is used to detect a specific antigen, antigen A, for which there are two monoclonal antibodies against different regions of the antigen. The first antibody is coupled with alkaline phosphatase whereas the second one is coupled with firefly luciferase. In the enzyme channeling system, the appropriate corresponding substrate is firefly luciferin O-phosphate. Therefore, a detection mix contains three key components (first antibody-alkaline phosphatase conjugate, second antibody-firefly luciferase conjugate, and firefly luciferin O-phosphate) and other appropriate conditions that enable the reactions to occur. Preferably, the detection mix is 1130 lyophilized to maintain long-term stability. In preferred embodiments, the detection mix also contains an antibody that binds to free firefly luciferin but not firefly luciferin O-phosphate, which reduces the background.

An example of the detection procedure is as follows: a sample from an appropriate source is diluted in a buffer (e.g., 1 mL of 1×PBS buffer), which is then added to the lyophilized detection mix in a detection tube. After thorough mixing, the detection tube is placed in a luminometer for detection. In the presence of antigen A, a sandwich structure similar to depicted in FIG. 16, thereby causing the firefly luciferase to be closed to the phosphatase. Close proximity of the two enzymes results in more efficient signal production, e.g., enhanced signal output, in comparison with the control that contains no antigen A (the analyte). This is because close proximity of the two enzyme causes the released free firefly luciferin to be immediately consumed by firefly luciferase to produce stronger light signal, which indicates the presence of the analyte. In particular, when there is a firefly luciferin-sequestering entity (e.g., firefly luciferin-binding protein) in the detection mix, the background is much lower, resulting in an enhanced signal to noise ratio.

In certain embodiments, the substrate (firefly luciferin O-phosphate) is not contained in the detection mix. In stead, the substrate is contained in the sample dilution buffer. This will prevent the substrate from being degraded during manufacturing, which may take several hours from formulation, dispensing to individual detection tube to lyophilization. In other embodiments, the firefly luciferin-binding antibody is also added to the sample dilution buffer along with the substrate, which may reduce the free firefly luciferin produced in the dilution buffer due to auto-cleavage of the substrate.

It is understood that concentration of various components in the detection mix (e.g., antibody—enzyme conjugates, firefly luciferin-binding antibody etc) need to be optimized, which can be performed using protocols well known to the skilled in the art.

EXAMPLE 8

Detecting of an Antigen Using a Firefly Luciferase Based Enzyme Channeling System In this example, ATP is used as a limiting factor for detection in the firefly luciferase based channeling system. When ATP producing enzyme is used in the system, no firefly luciferin-producing enzyme (e.g. phosphatase) labeled antibody is required. The first antibody is coupled to an ATP producing enzyme whereas the second antibody is coupled with the firefly luciferase. Free firefly luciferin is added in the detection mix in appropriate concentration.

In this example, the ATP-producing enzyme is pyruvate kinase, which converts ADP to ATP in the presence of phosphoenolpyruvate under appropriate conditions (e.g., pH, salt composition). Therefore, in this system, the substrates are ADT and phosphoenolpyruvate instead of the firefly luciferin O-phosphate described in Example 7. In order to decrease the background noise, an ATP degrading enzyme such as ATP hydrolysase can be added to the detection mix to degrade the ATP not produced in the two-enzyme complex. This is in contrast with the example described in Example 7, where firefly luciferin binding antibody is used to reduce the background. Essentially, the ATP degrading enzyme competes with firefly luciferase, the latter producing the light signal in a chemiluminescence reaction. When firefly luciferase forms a complex with the ATP-producing enzyme in the two enzyme channeling system, firefly luciferase is advantageous in competing for ATP because of its physical proximity to the ATP producing enzyme.

Detection of ATP with firefly luciferase is well established in the art for detection of microorganisms or contaminating biological tissues. The conditions are similar to what are described in Examples 1 and 2.

The detection mix can be formulated to contain all necessary reagents and chemicals for both enzymatic reactions except for ADP (one of the substrates) and ATP degrading enzyme, both of which are preferably, but not necessarily, contained in the sample dilution buffer (e.g., 1×PBS buffer).

For detection of antigen A, the detection mix contains the first antibody-pyruvate kinase conjugate, the second antibody-firefly luciferase conjugate, phosphoenolpyruvate, firefly luciferin, appropriate amounts of salts and pH conditions, 1% sucrose, and 8% mannitol. This detection mix is preferably lyophilized for long-term storage of the detection mix.

The sample dilution buffer may contain 1×PBS, appropriate amounts of ADP and appropriate amounts of ATP hydrolyase. Presence of ATP hydrolyase in the sample dilution buffer can also eliminate ATP that is likely present in a biological sample and in ADP reagent.

An example of the detection procedure is as follows: a sample from an appropriate source is diluted in the sample dilution buffer described above (e.g., 1:100 dilution). Incubation may be necessary to allow for the ATP in the sample to be degraded by ATP hydrolyase in the buffer. 1 mL of the diluted sample is then added to the lyophilized detection mix in a detection tube. After thorough mixing, the detection tube is placed in a luminometer for detection. In the presence of antigen A, a sandwich structure similar to that depicted in FIG. 22 is formed, thereby causing the firefly luciferase to be in close proximity to the pyruvate kinase. Being in close proximity to pyruvate kinase, which converts ADP to ATP, firefly luciferase can more effectively compete with ATP hydrolyase for ATP, thereby resulting in enhanced signal output when compared to the control that contains no antigen A (the analyte). Therefore, increased signal indicates the presence of the analyte.

EXAMPLE 9

Detection of Nucleic Acid Sequences, Peptides, and Small Molecules Using a Firefly Luciferase Based Enzyme Channeling System Detection of other analyte types such as peptides, small molecules and nucleic acids can also be performed using an enzyme channeling system or its variations described in the present invention. Hybridization of nucleic acid sequences can also be detected since they can form complex that brings the two-enzymes physically close together. In a system for detecting a nucleic acid sequence with two hybridization domains, the two enzymes can be coupled with two distinct probes, one for each domain. Presence of the target nucleic acid sequence will cause the two enzymes to be hybridized to the same nucleic acid sequence and therefore be in close proximity.

Sometimes small molecules that have only one ligand-binding domain can also be detected with the enzyme channeling system described in the current invention. Detection of small molecules with only one ligand-binding domain, however, requires a competition-based assay. For example, one of the enzymes (e.g., pyruvate kinase) is coupled with an antibody specific for the small molecule whereas the luciferase is coupled with the small molecule itself. When these two conjugates are mixed together in a detection mix along with substrates and under appropriate conditions, a signal is generated. When a sample containing the small molecule is added, the signal is reduced because the small molecule in the sample competes with those coupled to firefly luciferase for the antibody coupled to the other enzyme. When ATP producing enzyme is used in the system, ATP hyrolyase (or other ATPases) can be used to improve the signal to noise ratio. In this case, a reduction of the signal indicates the presence of analyte in the sample.

One detailed example is given below: the assay is to detect the peptide human chronic gonadotropin (hCG) in the serum sample. The first monoclonal antibody for human chronic gonadotropin (hCG) is linked with bacterial sialidase, the second monoclonal antibody for hCG, which recognizes a different portion of the hCG molecule than that recognized by the first monoclonal antibody is linked with firefly luciferase.

The detection solution contains the following:

| Imidazole (pH 7.0) | 50 mM |
| BSA | 1 mg/mL |
| ATP, Na Salt | 12 mM |
| DTT | 10 mM |
| Co-enzyme A | 1 mM or 10 mg/mL |
| MgSO4 | 15 mM |
| CaCl2 | 4 mM |
| Mannitol | 4% |
| Sucrose | 1% |
| Sodium Azide | 0.05% |
| Firefly Luciferase-antibody conjugate | 2 µg/mL |
| Sialidase-antibody conjugate | 2 µg/mL |

100 microliters of assay solution described above is mixed with 100 microliters of HCG containing sample and incubated at 25 degree C. for 10 minutes. Next, 100 microliters of substrate (N-acetylneuraminic acid-firefly luciferin conjugate, 50 micrograms/mL) solution is added to the reaction mix and placed in a luminometer for reading the light signal. The higher the light signal reading, the higher the HCG concentration is in the sample. It is preferred that a background signal is established by testing a large number (e.g., 50 samples) and a linear curve is established by testing serially diluted positive samples. It is preferred that an antibody against firefly luciferin is included in the detection mix to increase the signal to noise ratio.

Yet another more detailed example is given below: the assay is to detect a target nucleic acid sequence in a competition assay format. The target sequence is CCCCCCCCCCCC. Streptavidin agarose (from Invitrogen, Catalog Number SA100-04) is coated with biotin labeled firefly luciferase and biotin labeled DNA sequence GGGGGGGGGG-biotin by incubating the agarose beads with the biotinylated luciferase and DNA sequence. After washing to get rid of the excess firefly luciferase and GGGGGGGGGGGG-biotin, CCCCCCCCC-alkaline phosphatase conjugate is incubated with the bead and the resulting bead-GGGGGGGGG-CCCCCCCCC-alkaline phosphatase complex is again washed to get rid of the excess CCCCCCCCC-alkaline phosphatase conjugate. The resulting beads are called detection beads.

The assay formulation contains the following:

| Imidazole (pH 8) | 50 mM |
| BSA | 1 mg/mL |
| ATP, Na Salt | 12 mM |
| DTT | 10 mM |
| Co-enzyme A | 1 mM or 10 mg/mL |
| MgSO4 | 15 mM |
| CaCl2 | 4 mM |
| Mannitol | 4% |
| Sucrose | 1% |
| Sodium Azide | 0.05% |
| Detection beads | 2 µg/mL |

100 microliters of assay solution described above is mixed with 100 microliters of sample and incubated at 25 degree C. for 30 minutes. Next 100 microliters of substrate (firefly luciferin O-phosphate, 50 micrograms/mL) solution is added to the reaction mix and placed in a luminometer for reading the light signal. The lower the light signal reading, the higher the target nucleic acid concentration is in the sample. It is preferred that a background signal is established by testing a large number (e.g., 50 samples) and a linear curve is established by testing serially diluted positive samples. It is preferred that an antibody against firefly luciferase is included in the detection mix to increase the signal to noise ratio.

EXAMPLE 10

Detection of Human IgG from HIV Positive Serum Using a Firefly Luciferase Based Enzyme Channeling System The current example utilizes ATP producing enzyme-based enzyme channeling system. In the current example sulfate adenylyltransferase (ATPS) is used, which converts APS (adenosine 5'-phosphosulfate) to ATP in the presence of PPi, for generating ATP. The ATPS is fused with ZZ domain (ATPS-ZZ), which can bind with IgG. Another affinity ligand is gp160, which can bind with the HIV positive IgG. The ATP utilizing luciferase and one of the affinity ligand are co-immobilized on solid support. The firefly luciferase or click beetle luciferase is biotinylated. The gp160 is also biotinylated. Avidin coated EIA stripwell plate is coated with these biotin labeled firefly luciferase (or click beetle luciferase) and gp160. Some of the suitable ratio of coated firefly luciferase and coated gp160 is between 10:1 to 1:2. The coating of biotin labeled protein to avidin plate is well known to the skilled in the art and the biotinylated firefly luciferase and gp160 are commercially available. Each well is added with 50 ng of ATPS-ZZ in 150 uL PBS buffer containing 0.1% BSA as well as different amount of IgG. Incubation is performed for 20 min under room temperature. Next 50 uL HBA buffer is added to each well and the light signal is collected with a luminometer for 2 min. HBA buffer contains 0.1 M Tris-Acetate, pH 7.75; 2 mM EDTA, 10 mM Mg Acetate; 0.1% BSA; 1 mM DTT; 100 ug/ml D-Luciferin; 5 uM APS; 100 uM PPi; 0.25 mg/ml CoA and 0.4 mg/ml PVP. The reading of the well containing 10 ng of IgG is 5 times the reading of the well containing no IgG. In order to decrease the back ground, apyrase (from potato) can be added to the HBA buffer as ATP eliminating enzyme. One of the suitable concentration of apyrase in the final mix is 0.01~0.5 units/mL.

This assay can also be done without the need of solid phase support. In one embodiment, gp160 and firefly luciferase are conjugated directly without being immobilized on solid support. 25 ng of gp160-firefly luciferase conjugate and 50 ng of ATPS-ZZ in 200 uL PBS buffer containing 0.1% BSA are incubated together with different amount of IgG for 10 min. Next 50 uL HBA buffer is added and the light signal is collected with a luminometer for 2 min for the detection. The apyrase can also be added to reduce the background signal.

What is claimed is:

1. A kit for diagnosing renal diseases comprising firefly luciferin N-acetyl-beta-D-glucosaminide, DTT, Co-enzyme A, ATP, pH 5.0 citrate buffer and luciferase.

2. A kit for diagnosing renal diseases from urine sample comprising firefly luciferin N-acetyl-beta-D-glucosaminide, DTT, Co-enzyme A, ATP, pH 5.0 citrate buffer and luciferase.

3. A kit for detecting acute renal deficiency comprising firefly luciferin N-acetyl-beta-D-glucosaminide, DTT, Co-enzyme A, ATP, pH 5.0 citrate buffer and luciferase.

* * * * *